(12) United States Patent
Remmers et al.

(10) Patent No.: US 9,878,515 B2
(45) Date of Patent: Jan. 30, 2018

(54) PACKAGED HOT-MELT PRESSURE SENSITIVE ADHESIVE

(71) Applicant: H.B. FULLER COMPANY, St. Paul, MN (US)

(72) Inventors: Peter Remmers, Hamburg (DE); Dirk Laukien, Radbruch (DE); Lynne Purvis, Viborg (DK); Nicholas Porro, Wilmington, DE (US); Nicholas Taylor, Oakwood (GB)

(73) Assignee: H.B. Fuller Company, St. Paul, MN (US)

( * ) Notice: Subject to any disclaimer, the term of this patent is extended or adjusted under 35 U.S.C. 154(b) by 794 days.

(21) Appl. No.: 14/290,539

(22) Filed: May 29, 2014

(65) Prior Publication Data

US 2014/0356562 A1 Dec. 4, 2014

Related U.S. Application Data

(60) Provisional application No. 61/828,479, filed on May 29, 2013.

(51) Int. Cl.

| | |
|---|---|
| *B32B 1/02* | (2006.01) |
| *B65G 19/18* | (2006.01) |
| *C09J 7/02* | (2006.01) |
| *A61L 15/22* | (2006.01) |
| *A61L 31/04* | (2006.01) |
| *A61L 15/58* | (2006.01) |
| *A61L 31/14* | (2006.01) |
| *B32B 27/30* | (2006.01) |
| *B32B 1/08* | (2006.01) |
| *B32B 27/18* | (2006.01) |
| *B32B 27/22* | (2006.01) |
| *B32B 27/32* | (2006.01) |
| *B65G 27/00* | (2006.01) |
| *D06N 3/00* | (2006.01) |
| *D06N 3/04* | (2006.01) |
| *C09J 5/06* | (2006.01) |

(52) U.S. Cl.
CPC ............. *B32B 1/02* (2013.01); *A61L 15/225* (2013.01); *A61L 15/585* (2013.01); *A61L 31/041* (2013.01); *A61L 31/14* (2013.01); *B32B 1/08* (2013.01); *B32B 27/18* (2013.01); *B32B 27/22* (2013.01); *B32B 27/30* (2013.01); *B32B 27/306* (2013.01); *B32B 27/32* (2013.01); *B32B 27/325* (2013.01); *B32B 27/327* (2013.01); *B65G 19/18* (2013.01); *B65G 27/00* (2013.01); *C09J 5/06* (2013.01); *C09J 7/0221* (2013.01); *C09J 7/0275* (2013.01); *D06N 3/0011* (2013.01); *D06N 3/0086* (2013.01); *D06N 3/045* (2013.01); *C09J 2201/61* (2013.01); *C09J 2423/003* (2013.01); *D06N 2203/042* (2013.01); *D06N 2205/06* (2013.01); *D06N 2209/16* (2013.01); *D10B 2509/00* (2013.01); *D10B 2509/026* (2013.01); *Y10T 428/1334* (2015.01); *Y10T 428/1341* (2015.01); *Y10T 428/1352* (2015.01); *Y10T 428/1379* (2015.01); *Y10T 428/23* (2015.01); *Y10T 428/28* (2015.01); *Y10T 428/2967* (2015.01); *Y10T 442/2754* (2015.04)

(58) Field of Classification Search
CPC .. B32B 1/02; B32B 1/08; B32B 27/18; B32B 27/22; B32B 27/30; B32B 27/306; B32B 27/32; B32B 27/325; B32B 27/327; B65G 19/00; B65G 19/18
See application file for complete search history.

(56) References Cited

U.S. PATENT DOCUMENTS

| | | |
|---|---|---|
| 4,054,632 A | 10/1977 | Franke |
| 4,379,806 A | 4/1983 | Korpman |
| 4,490,424 A | 12/1984 | Gerace |
| 4,804,110 A | 2/1989 | Sperry et al. |
| 5,333,439 A * | 8/1994 | Bozich ................ B65D 65/42 206/447 |
| 5,373,682 A | 12/1994 | Hatfield |
| 5,669,207 A | 9/1997 | Hull |
| 5,804,610 A * | 9/1998 | Hamer ................ B29B 13/022 156/275.7 |
| 6,095,803 A | 8/2000 | Slater |
| 6,180,229 B1 | 1/2001 | Becker |
| 6,383,958 B1 | 5/2002 | Swanson et al. |
| 6,431,409 B1 | 8/2002 | Gehde |
| 6,624,273 B1 * | 9/2003 | Everaerts ............... C09J 131/02 427/508 |
| 7,572,494 B2 | 8/2009 | Mehta et al. |

(Continued)

FOREIGN PATENT DOCUMENTS

| | | |
|---|---|---|
| EP | 0 207 200 | 1/1987 |
| EP | 0 649 378 | 4/1995 |

(Continued)

*Primary Examiner* — Walter B Aughenbaugh

(74) *Attorney, Agent, or Firm* — Kristi Halloran; Kirsten Stone

(57) ABSTRACT

The present invention relates to a packaged hot-melt pressure sensitive adhesive comprising a hot-melt pressure sensitive adhesive composition and a coextrusion coating consisting of neat low density polyethylene, neat polypropylene, or neat ethylene vinyl acetate. The present invention further relates to the use of the packaged adhesive formed as individual forms in an adhesive application process, and the use of the packaged adhesive in the production of laminated articles, including nonwoven hygiene articles, disposable medical drapes, and also laminate constructions such as tapes and labels.

19 Claims, 2 Drawing Sheets

(56) References Cited

U.S. PATENT DOCUMENTS

| | | |
|---|---|---|
| 2003/0116259 A1 | 6/2003 | Sayovitz |
| 2010/0021630 A1 | 1/2010 | Makover et al. |
| 2010/0305259 A1 | 12/2010 | Rodriguez |
| 2013/0143997 A1 | 6/2013 | Burgsmuelier et al. |
| 2014/0311872 A1 | 10/2014 | Podevyn |

FOREIGN PATENT DOCUMENTS

| | | |
|---|---|---|
| EP | 0 469 564 | 11/1996 |
| FR | 2762308 | 10/1998 |
| WO | WO01/46019 | 6/2001 |
| WO | WO 01/79111 | 10/2001 |
| WO | WO2012/123282 | 9/2012 |

\* cited by examiner

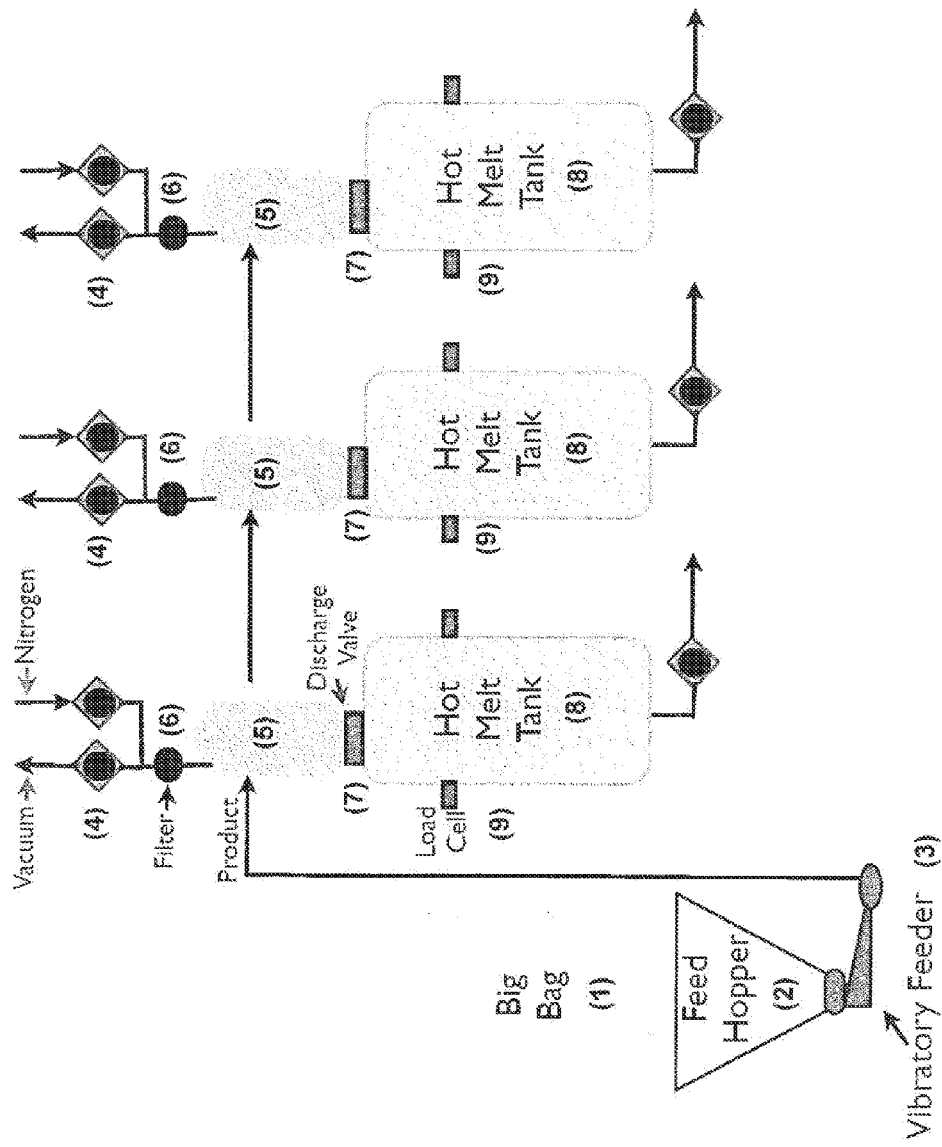
Figure 1: Vacuum-conveying system

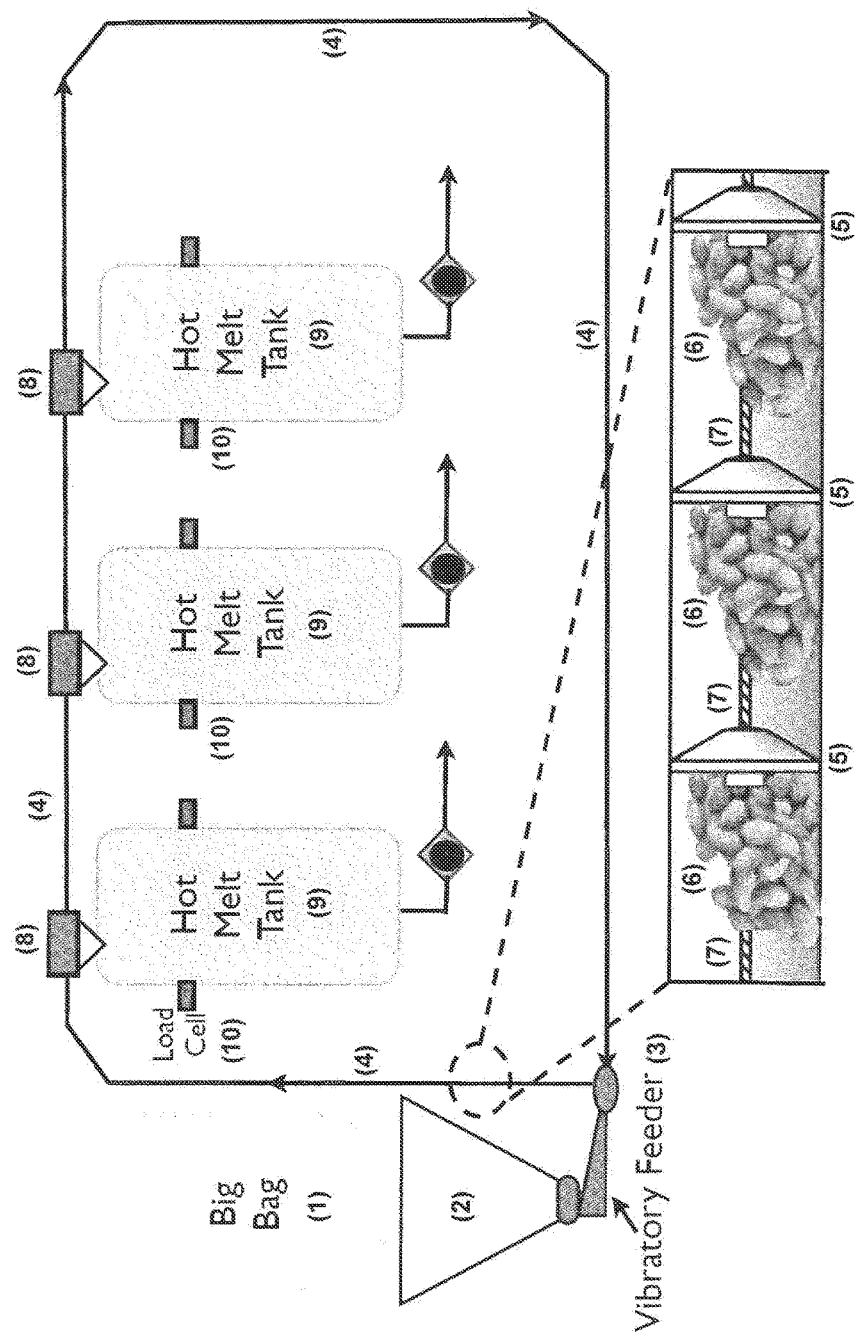

PACKAGED HOT-MELT PRESSURE SENSITIVE ADHESIVE

This patent application claims the benefit of or priority to U.S. provisional application No. 61/828,479 filed on May 29, 2013.

FIELD OF THE INVENTION

The present invention relates to a packaged hot-melt pressure sensitive adhesive comprising a hot-melt pressure sensitive adhesive composition and a coextrusion coating consisting of neat low density polyethylene, neat polypropylene, or neat ethylene vinyl acetate. The present invention further relates to the use of the packaged adhesive formed as individual forms in an adhesive application process, and the use of the packaged adhesive in the production of laminated articles, including nonwoven hygiene articles, disposable medical drapes, and also laminate constructions such as tapes and labels.

BACKGROUND OF THE INVENTION

Hot-melt adhesive compositions are typically solid at room temperature. Therefore, said adhesive compositions are heated and are subsequently applied to a substrate in a molten state, which is then placed in contact with one or more further substrates. The hot-melt adhesive composition cools and solidifies, thereby forming a bond between the substrates.

Hot-melt adhesive compositions can be used for a variety of industrial adhesive applications such as packaging and labeling, production of nonwoven hygiene and sanitary articles, such as for the bonding of elastics, construction and core lamination or positioning adhesive and also for other laminates such as tapes and labels.

To prevent hot-melt adhesive compositions from agglomerating prior to their intended use, said adhesive compositions are typically provided in a packaged form. Packaged hot-melt adhesives are typically composed of a base polymer, a tackifying agent and a wax component. The base polymer provides the formulation with its strength and adhesive characteristics. The tackifying agent allows the polymer to be more adhesive by improving wetting during the application, and give tack to the adhesive and also lower the viscosity. Tack is required in most adhesive formulations to allow for proper joining of articles prior to the hot-melt adhesive solidifying.

A great disadvantage of currently used packaged hot-melt pressure sensitive adhesives is that fusion of the several packaging materials increasingly leads to agglomeration of several particular forms during storage, which may lead to the blocking of said individual forms during the subsequent adhesive application processes. Such agglomeration may prevent the use of the individual forms, because it may be very difficult to remove the packaged hot-melt adhesive from the storage container, or it may prevent an automatic or semi automatic processing of the individual forms, e.g. pillows or prills, to be fed to the melting tanks. By automating this process, the customer will have significantly reduced handling and be able to store the adhesive at a further distance from the melt tank and convey with reduced operator requirement.

The packaging material of the hot-melt pressure sensitive adhesive typically includes various coating materials such as various portage linen blends and core polymers to avoid agglomeration. Currently, anti-blocking powders such as talc wax or silica are used in the discharge of hot-melts to avoid agglomeration. However, these compounds tend to become completely absorbed over time by the hot-melt and as a result, the residual tack reappears. Furthermore, some of the currently used anti-blocking agents such as silica dust are potentially harmful or can cause serious health issues, for example, lung or respiratory problems.

Packaged hot-melt pressure sensitive adhesives refer to adhesives, which form a bond when pressure is applied to attach the adhesives to the adhering substrates. Said pressure sensitive packaged adhesives are usually designed to properly attach to the adhering substrate at room temperature. Pressure sensitive adhesives have a tendency to fuse together at room temperature, which might lead to agglomeration of the pressure sensitive adhesive during normal handling and might therefore impair the use of the corresponding adhesives. To prevent such fusion and blocking of packaged hot-melt pressure sensitive adhesives, powder solutions are normally insufficient and said adhesives are typically packaged in more advanced coating material, e.g. a plastic or metal film.

U.S. Pat. No. 5,373,682 discloses a method for packaging hot-melt pressure sensitive adhesives into a plastic film. However, the method describes packaging a molten hot-melt adhesive into a solid plastic film and thereby does not disclosure a coextrusion process, wherein the adhesive composition and the coating are both applied in a molten state. A particular disadvantage of the process disclosed in U.S. Pat. No. 5,373,682 is that packaging of a molten hot-melt adhesive into a solid plastic film results in packaged adhesives, which are not uniformly packaged, e.g. which encompass air inclusions, which in turn may lead to an elevated blocking and fusion tendency of the packaged adhesives.

U.S. Pat. No. 7,572,494 B2 discloses a method for packaging hot-melt adhesives, in particular hot-melt pressure sensitive adhesives, which includes an extrusion process of a hot-melt adhesive and coextrusion of a wax-based polymeric film compositions to surround the hot-melt adhesive. However, the coextruded wax-based polymer coating consists of a polymer composition consisting of several different ingredients.

There remains a need in the art for packaged hot-melt pressure sensitive adhesives, which comprise anti-blocking coatings, which improve the handling of hot-melt adhesives and prevents agglomeration permanently and reliably.

SUMMARY OF THE INVENTION

It is an object of the present invention to provide a packaged hot-melt adhesive, specifically a hot-melt pressure sensitive adhesive composition, the individual forms of which do not fuse together or agglomerate during their packaging, transportation, storage or further processing. A further object is to provide free-flowing hot-melt pressure sensitive adhesives in individual form.

In one aspect of the invention, a packaged hot-melt adhesive is provided, comprising a hot-melt pressure sensitive adhesive composition (a) and a coextrusion coating (b) consisting of neat low-density polyethylene (LDPE), neat polypropylene, or neat ethylene vinyl acetate having a melt flow index between about 20 g/10 min and about 300 g/10 min (ASTM D 1238-190° C., 2.16 kgs).

In one embodiment of the present invention, the adhesive composition (a) comprises a base polymer selected from the group consisting of polyolefins, polyolefin copolymers, polyolefin/alpha-olefin interpolymers or synthetic rubbers.

In a preferred embodiment of the present invention, the adhesive composition (a) comprises a base polymer, which is selected from the group consisting of ethylene and propylene homo- or copolymers.

In a preferred embodiment, the adhesive composition (a) comprises a base polymer, selected as ethylene-octene copolymer.

In a preferred embodiment of the present invention, the adhesive composition (a) comprises a base polymer, which is selected as a metallocene-synthesized polymer, preferably as a single-site metallocene-synthesized polymer, more preferably as a metallocene-synthesized ethylene or propylene homo- or copolymer, even more preferably as a metallocene-synthesized polypropylene polymer.

In a preferred embodiment of the present invention, the adhesive composition (a) comprises a base polymer, which is selected as a metallocene-synthesized low molecular weight polypropylene polymer.

In a preferred embodiment of the present invention, the adhesive composition (a) comprises a base polymer, which is selected from the group consisting of styrene-isoprene (SI), styrene-isoprene-styrene (SIS), styrene-butadiene-styrene (SBS), styrene-ethylene/butylene-styrene (SEBS) or styrene-ethylene/propylene-styrene (SEPS).

A further object of the present invention is to provide packaged hot-melt adhesives which exhibit a low content of plasticizer to maintain an adhesive composition (a) which exhibits an increased hardness.

According to one embodiment of the present invention, the adhesive composition (a) additionally comprises one or more plasticizers in an amount of less than about 30 wt %, preferably less than about 20 wt %, more preferably less than about 15 wt %, even more preferably less than about 10 wt % and most preferably less than about 5 wt %, referring to the total weight of the packaged adhesive.

In one embodiment of the present invention, the adhesive composition (a) additionally comprises one or more tackifying agents in an amount between about 5 wt % and about 75 wt %, preferably between about 10 wt % and about 60 wt %, more preferably between about 15 wt % and about 50 wt %, referring to the total weight of the packaged adhesive.

An object of the present invention is to provide packaged hot-melt adhesives, which provide the packaged hot-melt adhesive with a reduced tackiness, while the other properties and the purity of the packaged hot-melt adhesive, i.e. the components of the hot-melt pressure sensitive adhesive composition remains unaffected. It is also an object of the present invention to provide hot-melt particular forms which are free-flowing and or have a substantially tack-free surface for extended periods of time.

In one embodiment of the present invention, the packaged hot-melt adhesive comprises a coating (b) in an amount between about 0.1 wt % and about 5 wt %, preferably between about 0.5 wt % and about 3 wt %, more preferably between about 1 wt % and about 2 wt %, and most preferably between about 1.5 wt % and about 5 wt %, referring to the total weight of the packaged adhesive.

In one embodiment of the present invention, the packaged hot-melt adhesive comprising a coating (b), wherein the melt flow index (ASTM D 1238-190° C., 2.16 kgs) of the coating (b) is between about 50 g/10 min and about 180 g/10 min, preferably between about 100 g/10 min and about 170 g/10 min and most preferably about 150 g/10 min.

In one embodiment of the present invention, the packaged hot-melt adhesive comprising a coating (b) has a melt temperature (Ring and Ball, DIN EN 1427) between about 60° C. and about 150° C., preferably between about 100° C. and about 140° C. and more preferably between about 120° C. and about 130° C.

In one embodiment of the present invention, the packaged hot-melt adhesive comprising a coating (b) has a room temperature density (ASTM D 1505) between about 0.80 g/cm$^3$ and about 1.00 g/cm$^3$, preferably between about 0.90 g/cm$^3$ and about 0.93 g/cm$^3$, and more preferably about 0.92 g/cm$^3$.

The packaged hot-melt adhesive according to the present invention encompasses a specific parameter range, which is advantageous for the beneficial properties of the inventive packaged hot-melt adhesive. Further advantageous embodiments of the present invention are defined in the corresponding dependent claims.

In one embodiment of the present invention, the adhesive composition (a) has an average penetration number (PZ), which is between about 5 and about 200, preferably between about 10 and about 100, more preferably between about 15 and about 80, and most preferably between about 20 and about 70.

Another object of the present invention is to provide individual forms of the packaged hot-melt adhesive, such as pillows or prills, as defined below, which do not agglomerate during packaging, transportation, storage or further processing.

It would also be desirable to prevent the agglomeration of packaged hot-melt adhesives permanently. Furthermore, it would be desirable to provide packaged hot-melt pressure sensitive adhesives, which allows easy de-agglomeration of temporarily blocked individual forms of the packed hot-melt adhesive, for example when high-pressure is applied to the packaged hot-melt adhesive during transportation or storage, or when the packed hot-melt adhesive is transported or stored at elevated room temperature, for example at an average temperature of between about 25° C. and about 45° C. between about 25° C. and about 65° C., or even of between about 25° C. and about 70° C.

A further object of the present invention is to provide a packaged hot-melt pressure sensitive adhesive, which does not undesirably change the characteristics of the packaged hot-melt adhesive after melting, such as bonding performance, melt viscosity, handling, etc.

A further object of the present invention is to provide a packaged hot-melt pressure sensitive adhesive, which is environmentally safe and which is not harmful to health.

The object of the present invention is the provision of packaged hot-melt adhesives, which do not agglomerate and thereby block during the specific application processes.

According to one embodiment, the packaged hot-melt adhesive is formed in a particular form, such as a pillow or prill.

Preferably, the particular forms, such as pillows or prills have dimensions (length/width/height) which are from about 40 mm×about 30 mm×about 12 mm, or about 20 mm×about 20 mm×about 20 mm, preferably about 40 mm×about 20 mm×about 10 mm and most preferably about 40 mm×about 15 mm×about 7 mm.

Preferably, a plurality of individual forms such as pillows or prills, do not fuse together and/or are mechanically separable to induce free-flowing of the individual forms.

Preferably, a plurality of individual forms of a packaged hot-melt adhesive, such as pillows or prills, is used in an adhesive application process, wherein the packaged hot-melt adhesive is conveyed to a melting system in a free-flowing and air conveyable form before being molten and applied to a substrate.

According to another embodiment, the packaged hot-melt adhesive is formed in a particular form, such as a coextruded rope.

Preferably the coextruded ropes have a diameter which is between about 0.1 cm and about 5 cm, preferably between about 1 cm and about 3 cm, and more preferably about 2.5 cm.

Preferably, a coextruded rope, is used in an adhesive application process, wherein the packaged hot-melt adhesive is conveyed to a melting system by pulling the coextruded rope through a series of pulleys inside a protective cover into the premelter.

Preferably, the plurality of individual forms such as a coextruded rope, do not fuse together and/or are mechanically separable to induce free-flowing of the individual forms.

For individual forms, the packaged hot-melt adhesive has a free-flowing and/or air-conveyable form at ambient conditions.

According to the invention, the package hot-melt adhesive is obtained by a coextrusion process.

Preferably, the packaged hot-melt adhesive according to the present invention is obtained by a coextrusion process, wherein the hot-melt pressure sensitive adhesive composition (a) is pumped through the coextrusion head and wherein the coextrusion coating (b) is added to the adhesive composition (a) such that the coextrusion coating (b) substantially covers the adhesive composition (a) as a cover sheet.

Furthermore, the packaged hot-melt adhesive is obtained by a coextrusion process, wherein the coextrusion process comprises:
  (i) providing one or more hot-melt components and blending the hot-melt components to form a hot-melt pressure sensitive adhesive composition
  (ii) providing a coating material selected from neat low-density polyethylene, neat polypropylene, or neat ethylene vinyl acetate having a melt flow index between about 20 g/10 min and about 300 g/10 min.
  (iii) coextruding both (i) and (ii) such that the adhesive forms a strand substantially surrounded by the coating material
  (iv) optionally cutting the resulting, coated strand of adhesive (e.g. by forcing the composition past rotating blades and cutting the hot-melt ribbons to form resultant individual forms)
  (v) solidifying the individuals, optionally by cooling the individuals by a liquid cooling medium or by a dry air circulated.

According to the invention, a coextruded packaged hot-melt pressure sensitive adhesive, obtained by a process wherein the hot-melt pressure sensitive adhesive composition (a) is pumped through a coextrusion head and wherein the coextrusion coating (b) is added to the adhesive composition (a) such that the coextrusion coating (b) substantially covers the adhesive composition (a) as a cover sheet and; wherein the hot-melt pressure sensitive adhesive composition has an average penetration number (PZ), which is between about 20 and about 70.

In one embodiment, the coextruded packaged hot-melt pressure sensitive adhesive is provided as a plurality of individual forms. In another embodiment, the plurality of individual forms of a packaged adhesive are used in an adhesive application process, wherein the packaged adhesive is conveyed to a melting system, then heated to a molten state in the melting system and applied to a substrate. In still another embodiment, the plurality of individual forms do not fuse together and/or are mechanically separable to induce free flowing of the individual forms prior to entering the melting system. In another embodiment, the plurality of individual forms is conveyed to a melting system by a conveying system selected from the group consisting of vacuum conveying, tubular drag conveying, big bag conveying and melt on demand conveying. In a different embodiment, the plurality of individual forms is conveyed to the melting system by a distribution system, which automatically distributes the plurality of forms to the melting system.

In another aspect of the invention, the adhesive containing container, comprising a plurality of individual forms of a packaged hot-melt pressure sensitive adhesive, wherein the container is selected from the group consisting of a box, a plastic bag, a pouch, a big bag, and a supersack; and wherein the hot melt pressure sensitive adhesive has an average penetration number (PZ), which is between about 20 and about 70.

In a preferred use of the invention, the packaged hot-melt adhesive is used for the production of hygiene and sanitary articles, non-woven articles, labeling, elastic lamination, construction lamination or as positioning adhesive. Preferably, the packaged hot-melt adhesive is used for the production of nonwoven hygiene articles including the production of diapers, adult incontinence devices, sanitary napkins, medical drapes and also laminate constructions such as tapes and labels.

In one aspect, the present invention is directed to an adhesive containing container comprising a plurality of individual forms of the packaged hot-melt adhesive according to the present invention, wherein the container is selected from at least one of a box, preferably a plastic bag, a pouch, a big bag, and a supersack.

FIGURES

FIG. 1: Schematic representation of a vacuum-conveying system.

Packaged hot-melt pressure sensitive adhesive is inserted into a feed hopper, is introduced into the vacuum-conveying system by a vibratory feeder and is filled into a series of hot-melt tanks, through a discharge valve, which is controlled by electronic level probes.

FIG. 2: Schematic representation of a tubular drag-conveying system.

Packaged hot-melt pressure sensitive adhesive is inserted into a tubular drag-conveying system by a vibratory feeder, wherein the adhesive is conveyed to a plurality of hot-melt tanks by a disc-distribution system, which is controlled by electronic level probes.

DETAILED DESCRIPTION OF THE INVENTION

In one aspect of the present invention, a packaged hot-melt adhesive is provided, comprising a hot-melt pressure sensitive adhesive composition (a) and a coextrusion coating (b) consisting of neat low-density polyethylene, neat polypropylene, or neat ethylene vinyl acetate having a melt flow index between about 20 g/10 min and about 300 g/10 min.

In a further aspect of the present invention, a plurality of individual forms of a packaged adhesive in accordance with the present invention are provided, which may be used in an adhesive application process, wherein the packaged adhesive is conveyed to a melting system in a free-flowing and air conveyable form before being molten and applied to a substrate.

In the following, the hot-melt pressure sensitive adhesive composition (a) and the coextrusion coating (b), and the anti-blocking characteristics of the packaged hot-melt adhesive, e.g. the individual forms, will be described in more detail, as well as individual forms comprising said packaged hot-melt adhesive.

Unless otherwise specified, the following abbreviations and definitions are used in the context of the present invention.

The undefined article "a" or "an" means one or more of the species designated by the term following said article. For example, "a individual form" encompasses one or more individual forms.

The term "about" in the context of the present application means a value within 15% (±15%) of the value recited immediately after the term "about," including any numeric value within this range, the value equal to the upper limit (i.e., +15%) and the value equal to the lower limit (i.e., −15%) of this range. For example, the phrase "about 100" encompasses any numeric value that is between 85 and 115, including 85 and 115 (with the exception of "about 100%", which always has an upper limit of 100%). A further exception is the phrase "about 0" or "about 0%", which always has a lower limit of 0 or 0%). In a preferred aspect, "about" means±10%, even more preferably ±5%, even more preferably ±1% or less than ±1%.

The amount of a specific component, which is added to packaged hot-melt adhesive comprising a hot-melt pressure sensitive adhesive composition (a) and a coextrusion coating (b) may be defined as the weight per weight percentage as defined by the following ratio: wt %=(g of specific component)/(g of composition comprising specific components). For example, when 2.5 g of plasticizer in 100 g of a packaged hot-melt adhesive are used, this results in a ratio of 2.5 wt % (2.5/100) of plasticizer.

For the purpose of the present invention, the term "hot-melt" or "hot-melt composition" refers to a solvent free product which is more or less solid at room temperature, e.g. at a temperature between about 20° C. and about 25° C. When heated the hot-melt becomes tacky and preferably liquid (molten) and can be applied, for example to a substrate to provide an adhesive surface.

The hot-melt adhesive composition (a) of the present invention is a hot-melt "pressure sensitive adhesive" composition. The term "pressure-sensitive adhesive" means an adhesive that is aggressively and permanently tacky at room temperature and firmly adheres to a variety of dissimilar surfaces upon mere contact without the need of more than finger or hand pressure, i.e. a hot-melt adhesive composition that retains surface tackiness over time including when cooled.

A. The Hot-Melt Pressure Sensitive Adhesive Composition (a)

A hot-melt pressure sensitive adhesive typically comprises at least one thermoplastic base polymer, at least one plasticizer and at least one tackifying agent.

Generally, the invention's hot-melts will additionally contain one or more tackifying resins, plasticizers or oils and optionally waxes plus customary additives and adjutants such as stabilizers, antioxidants, pigments, UV stabilizers or absorbers, fillers etc. Materials used in hot-melt adhesives are known.

The packaged hot-melt adhesive according to the present invention comprises a hot-melt pressure sensitive adhesive composition (a), which predominantly determines the adhesive properties of the packaged hot-melt adhesive.

The hot-melt pressure sensitive adhesive composition (a) comprises a base polymer. The present invention is not specifically limited with respect to the base polymer being used. Rather, any polymer that in principle can be used in hot-melt compositions is suitable according to the present invention. Typically, base polymers include thermoplastic polymers selected from e.g. polyolefins, polyolefin copolymers or polyolefin/alpha-olefin interpolymers, as well as amorphous poly-α-olefins such as atactic propylene, and propylene copolymers with ethylene, butene, hexene, and octane, or ethylene and propylene homo- or copolymers and mixtures thereof. Also useful are polyamides and polyesters, polyurethanes, or synthetic rubbers, such as styrene block copolymers.

The hot-melt pressure sensitive adhesive composition (a) will preferably comprise at least one ethylene polymer, and may comprise a blend of two or more polymers. The term ethylene polymer as used herein refers to homopolymers, copolymers and terpolymers of ethylene.

In the present invention, the base polymer can be selected from the group consisting of ethylene copolymers. In a preferred embodiment, the base polymer is selected as ethylene vinyl acetate, ethylene methyl acrylate, ethylene n-butyl acrylate, ethylene n-hexyl acrylate, ethylene-2-ethylhexyl acrylate, ethylene butene, ethylene octene, ethylene acrylic acid, or ethylene methacrylic acid copolymers. Even more preferred, the base polymer is selected as ethylene-octene copolymer.

Also, the base polymer is selected from the group consisting of polyolefin/alpha-olefin interpolymers, in particular ethylene copolymers, such as ethylene-octene. A particular preferred polymer such as ethylene octene has a melt flow index between about 0.1 g/10 min and about 4,000 g/10 min, preferably between about 1 g/10 min and about 10 g/10 min and most preferably about 5 g/10 min. A particular preferred polymer such as ethylene octene has a density between about 0.7 g/cm$^3$ and about 1.0 g/cm$^3$, preferably between about 0.8 g/cm$^3$ and about 0.9 g/cm$^3$, most preferably about 0.87 g/cm$^3$. More than one ethylene copolymer may be used to optimize the melt flow index and density of the polymer. A preferred example of ethylene copolymer includes ENGAGE 8200 available from Dow Chemical Company, US. A second polymer may be added in addition to the first to further optimize properties e.g. an ethylene vinyl acetate polymer may be used in combination with ethylene octene.

In another option of the present invention, the base polymer can be selected as a low molecular weight polypropylene polymer. These base polymers can either be homopolymers of propylene or copolymers of propylene with one or more α-olefin comonomer, such as for example ethylene, 1-butene, 1-hexene, or 1-octene. The average molecular weight of the low molecular weight polypropylene polymers in the scope of the present invention may be in the range between about 4,000 g/mol and about 150,000 g/mol, preferably between about 10,000 g/mol and about 100,000 g/mol, more preferably between about 30,000 g/mol and about 60,000 g/mol and most preferably about 45,000 g/mol. Said polymers may have a Vicat softening point between about 80° C. and about 170° C., preferably about 90° C. Polypropylene polymers are usually predominantly amorphous without a well-defined melting point. Preferred examples of polypropylene homopolymers or copolymers of propylene include VISTAMAX 6202 available from EXXON MOBILE CHEMICALS, US and MODU S-400 available from Idemitsu Kosan Co., JP.

Other polymers that may be useful in the hot-melt composition of the present invention include so-called metallocene or single-site catalyzed polymers, including homopolymers and interpolymers of ethylene, propylene, or butane including homopolymers and interpolymers of ethylene with at least one $C_2$ to $C_{20}$-α-olefin. In a preferred option, the basic polymer is selected as a metallocene-synthesized low molecular weight polypropylene polymer. Metallocene polymers are prepared using a constrained geometry or single site metallocene catalyst. Useful metallocene polymers include, e.g. a homogeneous linear or substantially linear polymers that are interpolymers of ethylene and at least one $C_3$-$C_{20}$-α-olefin including e.g., ethylene/α-olefin/diene terpolymers. The term "homogenous" as used with respect to the metallocene polymer indicates that any comonomer is randomly distributed within a given interpolymer molecule and substantially all of the interpolymer molecules have the same ethylene/comonomer ratio within that interpolymer. Linear ethylene interpolymers are interpolymers that have an interpolymer backbone substituted with less than 0.01 long chain branches per 1000 carbons. The substantially linear ethylene interpolymers are interpolymers that include long chain branching. The long chain branches have the same comonomer distribution as the polymer backbone and can be as long as about the same length as the length of the polymer backbone. Suitable substantially linear ethylene interpolymers have a polymer backbone substituted with from about 0.1 to about 3 long chain branches per 1000 carbons. Useful $C_3$-$C_{20}$-α-olefins used in the preparation of ethylene interpolymers include, e.g., propylene, isobutylene, 1-butene, 1-hexene, 4-methyl-1-pentene, 1-heptene, 1-octene, cyclopentene, cyclohexene, cyclooctene and combinations thereof. The dienes suitable as comonomers, particularly in the making of ethylene/α-olefin/diene terpolymers, are typically non-conjugated dienes having from 6 to 15 carbon atoms. Useful examples of suitable non-conjugated dienes include: (1) straight chain acyclic dienes including, e.g., 1,4-hexadiene, 1,5-heptadiene, and 1,6-octadiene; (2) branched chain acyclic dienes including, e.g., 5-methyl-1,4-hexadiene, 3,7-dimethyl-1,6-octadiene, and 3,7-dimethyl-1,7-octadiene, (3) single ring alicyclic dienes including, e.g., 4-vinylcyclohexene, 1-allyl-4-isopropylidene cyclohexane, 3-allylcyclopentene, 4-allyl cyclohexene, and 1-isopropenyl-4-butenylcyclohexene; and (4) multi-ring alicyclic fused and bridged ring dienes including, e.g., dicyclopentadiene, and cycloalkylidene-substituted norbornenes including, e.g., 5-methylene-2-norboraene, 5-methylene-6-methyl-2-norbornene, 5-methylene-6,6-dimethyl-2-norbornene, 5-propenyl-2-norbornene, 5-(3-cyclopentenyl)-2-norbornene, 5-ethylidene-2-norbornene, and 5-cyclohexylidene-2-norbornene. Useful homogenous linear or substantially linear ethylene polymers have a narrow molecular weight distribution ($M_w/M_n$) including, e.g., from 1.5 to 3.5, or even from 1.8 to 2.8.

Examples of useful metallocene polymers are described in U.S. Pat. Nos. 5,324,800, 5,548,014, 5,530,054 and 6,207,748 and incorporated herein.

Useful metallocene polymers are commercially available under the AFFINITY series of trade designations including EG 8200 polyolefin plastomer from Dow Chemical Company (Midland, Mich.), and linear ethylene polymers are commercially available under the EXACT series of trade designations from ExxonMobil (Texas).

The metallocene polymer is preferably present in the hot-melt adhesive composition in an amount from about 0% wt % to about 80 wt %, from about 5% wt % to about 70 wt %, from about 10 wt % to about 60 wt %, or even from about 15 wt % to about 50 wt %. In some embodiments the amount of metallocene polymer, which is present in the hot-melt adhesive composition may be higher, preferably up to about 90 wt % and more preferably the hot-melt adhesive composition may be neat metallocene polymer.

Metallocene polymer present in the adhesive composition (a) may exhibit some degree of crystallinity. For example, there are some grades of commercial low molecular weight polypropylene polymers having a low degree of crystallinity. Preferably, the adhesive composition (a) has a low degree of crystallinity and the coextrusion coating (b) according to the present invention has a high degree of crystallinity.

One other class of thermoplastic base polymers suitable for use in the pressure-sensitive hot-melt adhesive composition (a) together with the coextrusion coating (b) is thermoplastic elastomers. Suitable thermoplastic elastomers include block copolymers having at least one A block that includes a vinyl aromatic compound and at least one B block that includes an elastomeric conjugated diene, including hydrogenated, unhydrogenated conjugated dienes, and combinations thereof. The A blocks and the B blocks may bind to one another in any manner of binding such that the resulting copolymer is random, block, straight-chained, branched, radial, or a combination thereof. The block copolymer can exhibit any form including, e.g., linear A-B block, linear A-B-A block, linear A-(B-A)n-B multi-block, and radial (A-B)n-Y block where Y is a multivalent compound and n is an integer of at least 3, tetrablock copolymer, e.g., A-B-A-B, and pentablock copolymers having a structure of A-B-A-B-A. The adhesive composition can include blends of at least two different block copolymers.

Useful vinyl aromatic compounds include, e.g., styrene, alpha-methylstyrene, o-methylstyrene, m-methylstyrene, p-methylstyrene, p-tert-butylstyrene, 2,4-dimethylstyrene, 2,4,6-trimethylstyrene, diphenylethylenes including stilbene, vinyl naphthalene, vinylanthracene, vinyltoluene (a mixture of meta- and para-isomers of methylstyrene), vinylxylene, and combinations thereof. Suitable conjugated dienes include, e.g., butadiene (e.g., polybutadiene), isoprene (e.g., polyisoprene), 2,3-dimethyl-1,3-butadiene, 1,3-pentadiene, 1,3-hexadiene, and combinations thereof, and hydrogenated versions thereof including, e.g., ethylene, propylene, butylene and combinations thereof.

Useful block copolymers include polyvinyl aromatic in an amount between about 0 wt % and about 50 wt %, between about 5 wt % and about 50 wt %, between about 15 wt % and about 35 wt %, or even between about 20 wt % and about 30 wt %. Suitable block copolymers have a melt flow index between about 3 g/10 min and about 50 g/10 min, or between about 5 g/10 min and about 20 g/10 min, as determined by ASTM-D 1238.

The A block can also include a small amount (e.g. no greater than 10 wt % based on the weight of the A block) of a structural unit derived from unsaturated monomers other than the vinyl aromatic compounds including, e.g., 1-butene, pentene, hexene, butadiene, isoprene, methyl vinyl ether, methyl methacrylate, vinyl acetate and combinations thereof. The B block can also include a small amount (e.g., no greater than 10 wt % based on the amount of the B block) of a structural unit derived from unsaturated monomers other than the conjugated diene including, e.g., 1-butene, 1-pentene, 1-hexene, methyl vinyl ether, styrene, methyl methacrylate, and combinations thereof.

Useful elastomeric polymers include, e.g., rubber (polyisoprene), polybutadiene, synthetic polyisoprene, random styrene-butadiene polymers, styrene-butadiene block copolymers, multiarmed and repeating styrene-butadiene copolymers, styrene-butadiene-styrene block copolymers, styrene-isoprene block copolymers, styrene-isoprene-styrene block copolymers, styrene-multiarmed styrene-isoprene $(SI)_x$ block copolymers, styrene-ethylene-butylene-styrene block copolymers, styrene-isobutylene-styrene block copolymers, styrene-ethylene-ethylene-propylene-styrene block copolymers, styrene-ethylene-propylene-styrene block copolymers and combinations thereof.

Useful block copolymers are commercially available under the KRATON D and G series of trade designations from Shell Chemical Company (Houston, Tex.) including, e.g., KRATON D 1163 and 1117 and KRATON G 1652 and 1726, EUROPRENE Sol T trade designation from EniChem (Houston, Tex.), SEPTON trade designation from Septon Company of America (Pasadena, Tex.) including SEPTON S 1001 styrene-ethylene-propylene-styrene block copolymer, and SEPTON 4030, 4033, 4044, 4055 and 4077 block copolymers, and VECTOR series of trade designations from Dexco (Houston, Tex.) including VECTOR 4211 styrene-isoprene -styrene block copolymer.

The elastomer is present in the adhesive composition in an amount between about 0 wt % and about 35 wt %, between about 5 wt % and about 35 wt %, between about 10 wt % and about 30 wt %, or even between about 15 wt % and about 25 wt %.

Alternatively, the base polymer can be selected from the group consisting of synthetic rubbers. Preferably, the base polymer is selected from the group consisting of butadiene styrene, styrene-acrylonitrile, acrylonitrile-butadiene-styrene, styrene-butadiene rubbers, butadiene-styrene elastomers, styrene-isoprene (SI), styrene-isoprene-styrene (SIS), styrene-butadiene-styrene (SBS), styrene-ethylene/butylene-styrene (SEBS) or styrene-ethylene/propylene-styrene (SEPS). More preferred, the base polymer is selected from the group consisting of styrene-isoprene (SI), styrene-isoprene-styrene (SIS), styrene-butadiene-styrene (SBS), styrene-ethylene/butylene-styrene (SEBS) or styrene-ethylene/propylene-styrene (SEPS).

In a preferred embodiment the synthetic rubbers have melt flow index between about 0.1 g/10 min and about 4,000 g/10 min, preferably between about 10 g/10 min and about 60 g/10 min and most preferably between about 25 g/10 min and about 40 g/10 min. A particular preferred polymer such as styrene-isoprene (SI) or styrene-isoprene-styrene (SIS) has a density between about 0.8 g/cm$^3$ and about 1.0 g/cm$^3$, preferably between about 0.92 g/cm$^3$ and about 0.96 g/cm$^3$. More than one styrene-isoprene (SI) or styrene-isoprene-styrene (SIS) may be used to optimize the melt flow index and density of the polymer. Preferred examples of styrene-isoprene (SI) or styrene-isoprene-styrene (SIS) include KRATON D 117 and KRATON DI 1161 NS, available from Kraton Polymers, US, VECTOR 4114A and VECTOR 4411 A from Dexco Polymers, USA.

The base polymers according to the present invention may be functionalized, e.g. by using (co-)monomers with at least one functional group, e.g. by an unsaturated monomer, which is functionalized by carboxylic acids, dicarboxylic acids, organic esters, organic anhydrides, organic alcohols, organic acid halides, organic peroxides, amides or imides.

An object of the present invention is to provide a packaged hot-melt adhesive, which provides an increased structural resistance of the adhesive, which is referred hereto as hardness.

A measure of the hardness of a specific material is obtained by allowing a weighted needle of specified dimensions to penetrate into the material under specific test conditions, e.g. at a defined temperature. The penetration number (PZ) is usually recorded as the number of units of depth which the needle penetrates in a given time. The harder a specific material, the lower is its penetration number. The penetration number according to the present invention is determined by needle penetration according to the test procedure is described in DIN 51579 at a temperature of 25° C. (see also examples section).

In accordance with the present invention, the packaged hot-melt adhesive has an average penetration number (PZ), which is between about 5 and about 200, preferably between about 10 and about 100, more preferably between about 15 and about 80, and most preferably between about 20 and about 70.

Another parameter to determine the properties of a packaged hot-melt adhesive according to the present invention is the viscosity. Typically polymers partially display non-Newtonian viscosity properties. This means that their viscosity does not remain constant over a given range of shear rates. Polymer viscosity rates are typically referred to in correlation with the corresponding temperature, wherein said viscosity rates have been measured. The polymer viscosity according to the present invention is determined according to method ASTM D-3236 (see also examples section).

The hot-melt pressure sensitive adhesive composition (a) according to the present invention can be formulated to exhibit a suitable viscosity. Useful packaged hot-melt adhesives according to the present invention exhibit a viscosity measured at 150° C. of between about 200 mPas and about 20,000 mPas, preferably between about 500 mPas and about 10,000 mPas, more preferably between about 100 mPas and about 5,000 mPas and most preferably between about 2,000 mPas and about 4,000 mPas.

The packaged hot-melt adhesive according to the present invention comprises a hot-melt pressure sensitive adhesive composition (a) and a coextrusion coating (b), which typically consist of different materials, which in turn may have different viscosities.

The packaged hot-melt adhesive according to the present invention is characterized by various parameters. The melting point of the packaged adhesive according to the present invention is determined by the Ring and Ball method (DIN EN 1427) (see Example section).

The packaged adhesive according to the present invention may have a melting point according to DIN EN 1427 between about 60° C. and about 130° C., preferably between about 70° C. and 110° C.

Also, the packaged adhesive according to the present invention may have a density between about 0.80 g/cm$^3$ and about 1.00 g/cm$^3$, preferably between about 0.85 g/cm$^3$ and about 0.95 g/cm$^3$ and more preferably about 0.91 g/cm$^3$.

The packaged hot-melt adhesive comprising a hot-melt pressure sensitive adhesive composition (a) may additionally comprise further, optional, additives such as tackifying agents, plasticizers, stabilizers, antioxidants, pigments, dyes, ultraviolet light absorbers, anti-slip agents and combinations thereof.

In one aspect of the present invention, the packaged hot-melt adhesive comprising a hot-melt pressure sensitive adhesive composition (a) and a coextrusion coating (b) additionally comprises one or more plasticizers.

Suitable plasticizers may include naphthenic oils, paraffinic oils (e.g., cycloparaffin oils), mineral based oils, phthalate esters, adipate esters, olefin oligomers (e.g., oligomers of polypropylene, polybutene, and hydrogenated polyisoprene), polybutenes, polyisoprene, hydrogenated polyisoprene, polybutadiene, benzoate esters, animal oil, plant oils (e.g. castor oil, soybean oil), derivatives of oils, glycerol esters of fatty acids, polyesters, polyethers, lactic acid derivatives and combinations thereof. A "plasticizer" in the meaning of the present invention is a typically organic composition that can be added to thermoplastics, rubbers and other resins to improve extrudability, flexibility, workability and stretchability in the finished adhesive. Any material which flows at ambient temperatures and is compatible with the block copolymer may be useful. The most commonly used plasticizers are oils which are primarily hydrocarbon oils that are low in aromatic content and are paraffinic or naphthenic in character. The oils are preferably low in volatility, transparent and have as little color and odor as possible. Furthermore, olefin oligomers, low molecular weight polymers, vegetable oils and their derivatives and similar plasticizing oils may be used as plasticizers.

Also, the plasticizer can be selected from the group consisting of napthenic process oils and paraffinic process oils, such as NYFLEX 222B available from Nynas AB, SE and KRYSTOL 550 available from Petrochem Carless Ltd., UK.

Useful commercially available plasticizers include KAYDOL OIL from Sonneborn (Tarrytown N.Y.) PARAPOL polybutene from Exxon Mobil Chemical Company (Houston, Tex.), OPPANOL polyisobutylene from BASF (Ludwigsjhafen. Germany), KRYSTOL 550 mineral oil from Petrochem Carless Limited (Surrey, England) and PURETOL 15 mineral oil from Petro Canada Lubricants Inc. (Mississauga, Ontario).

Preferably, the amount of plasticizer in the hot-melt pressure sensitive adhesive composition (a) is less than about 30 wt % referring to the total weight of the packaged hot-melt adhesive, more preferably less than about 20 wt %, even more preferably less than about 15 wt %, even more preferably less than about 10 wt %, and most preferably less than about 5 wt %.

The packaged hot-melt adhesive comprising a hot-melt pressure sensitive adhesive composition (a) and a coextrusion coating (b) may additionally or alternatively comprise one or more tackifying agents.

The tackifying agent can be at least partially hydrogenated in order to improve stability for bulk handling. Useful tackifying agents have Ring and Ball softening point of less than about 140° C., less than about 130° C., less than about 100° C., or even between about 100° C. to about 140° C. The tackifying agent can be fluid or solid at room temperature. Suitable classes of tackifying agents include, e.g., aromatic, aliphatic and cycloaliphatic hydrocarbon resins, mixed aromatic and aliphatic modified hydrocarbon resins, aromatic modified aliphatic hydrocarbon resins, and hydrogenated versions thereof; terpenes, modified terpenes and hydrogenated versions thereof; natural rosins, modified rosins, rosin esters, and hydrogenated versions thereof: low molecular weight polylactic acid; and combinations thereof. Examples of useful natural and modified rosins include gum rosin, wood rosin, tall oil rosin, distilled rosin, hydrogenated rosin, dimerized rosin and polymerized rosin. Examples of useful rosin esters include e.g., glycerol esters of pale wood rosin, glycerol esters of hydrogenated rosin, glycerol esters of polymerized rosin, pentaerythritol esters of natural and modified rosins including pentaerythritol esters of pale wood rosin, pentaerythritol esters of hydrogenated rosin, pentaerythritol esters of tall oil rosin, and phenolic-modified pentaerythritol esters of rosin.

Examples of useful polyterpene resins include polyterpene resins having a melting point, as determined by DIN EN 1427 (Ring and Ball) of from about 10° C. to about 180° C., hydrogenated polyterpene resins, and copolymers and terpolymers of natural terpenes (e.g. styrene-terpene, alpha-methyl styrene-terpene and vinyl toluene-terpene). Examples of useful aliphatic and cycloaliphatic petroleum hydrocarbon resins include aliphatic and cycloaliphatic petroleum hydrocarbon resins having Ring and Ball softening points of from about 10° C. to about 140° C. (e.g., branched and unbranched C5 resins, C9 resins, and C10 resins) and the hydrogenated derivatives thereof.

Useful tackifying agents are commercially available under a variety of trade designations including, e.g., the ESCOREZ series of trade designations from Exxon Mobil Chemical Company (Houston, Tex.) including ESCOREZ 1310 LC, ESCOREZ 5400, ESCOREZ 5415, ESCOREZ 5600, ESCOREZ 5615, and ESCOREZ 5690, the EASTOTAC series of trade designations from Eastman Chemical (Kingsport, Tenn.) including EASTOTAC H-100R, EASTOTAC H-100L, and EASTOTAC H130W, the WINGTACK series of trade designations from Cray Valley HSC (Exton, Pa.) including WINGTACK 86, WINGTACK EXTRA, and WINGTACK 95, the PICCOTAC and KRISTALEX series of trade designations from Eastman Chemical Company (Kingsport, Tenn.) including, e.g., PICCOTAC 8095 and KRISTALEX 3100, ARKON M-100 of trade designations from Arakawa Europe GmbH, Germany, SUKOREZ SU-100 of trade designations from Kolon Industries Inc., Korea, and SYLVARES 7115 and SYLVARES SA 140 of trade designatons from Arizona Chemical, USA.

Preferably, the amount of tackifying agent in the hot-melt pressure sensitive adhesive composition (a) is between about 5 wt % and about 75 wt %, preferably between about 10 wt % and about 60 wt %, more preferably between about 15 wt % and about 50 wt %, referring to the total weight of the packaged adhesive.

The packaged hot-melt adhesive comprising a hot-melt pressure sensitive adhesive composition (a) and a coextrusion coating (b) may additionally or alternatively comprise one or more antixodiants and/or more stabilizers.

Useful antioxidants are, e.g., high molecular weight hindered phenols and multifunctional phenols. Useful stabilizers are, e.g., phosphites, such as tris-(p-nonylphenyl)-phosphite (TNPP) and bis(2,4-di-tert-butylphenyl)4,4'-diphenylene-diphosphonite and di-stearyl-3,3'-thiodipropionate (DSTDP). Useful antioxidants are, e.g., commercially available under trade designation IRGANOX, including IRGANOX 1010, from Ciba (Tenytown, N.Y.), and under the trade designation BNX, including BXN 1010, from Mayzo, Inc. (Norcross, Ga.). Useful anti-slip agents are, e.g., silicone oils. Examples thereof are commercially available, e.g., under the trade designation Tegiloxan and available from Goldschmidt Industrial Specialties.

The amount of antioxidant and/or stabilizer in the hot-melt pressure sensitive adhesive composition (a) may be between about 0.1 wt % and about 5.0 wt % referring to the total weight of the packaged hot-melt adhesive, more between about 0.1 wt % and about 3.0 wt %, more preferably between about 0.1 wt % and about 2.0 wt % even more preferably less than about 0.2 wt % and about 1 wt %.

B. The Coextrusion Coating (b)

According to the present invention, the packaged hot-melt adhesive comprises a coextrusion coating (b), which provides for the anti-blocking properties of the packaged hot-melt adhesive.

The inventors surprisingly found out that the coextrusion coating (b) as defined in the present invention, which is made of neat polymers instead of conventionally used compounded coextrusion material, effectively prevents the agglomeration of packaged hot-melt adhesives, e.g. individual forms, over extended periods of time. Furthermore, the addition of a coextrusion coating (b) to a hot-melt pressure sensitive adhesive composition (a) allows for an easy de-agglomeration of potentially blocked individual forms. It was also found that coextruded coatings (b) are particularly useful for the anti-blocking properties of polyolefins, polyolefin copolymers or polyolefin/alpha-olefin interpolymers, as well as amorphous poly-α-olefins, which typically possess some residual or permanent tack, particularly at elevated ambient temperatures. In particular, the inventors found that the anti-blocking properties of the coextrusion coating (b) of the packaged hot-melt adhesive are not adversely affected when the hot-melt is exposed to higher ambient temperatures (e.g. between about 25° C. and about 70° C.), for example during storage or transportation. This makes the anti-blocking properties of the inventive coextrusion coating (b) very reliable.

To provide hot-melt pressure sensitive adhesives with anti-blocking properties, powdered coating materials or compounded coextrusion coating are conventionally applied.

Powdered coating materials are conventionally loaded onto the hot-melt pressure sensitive adhesive in a subsequent step after adhesive formation. A major problem for hot-melt pressure sensitive adhesives with powdered coating materials is that the diffusion of the components of the powdered coating material into the adhesive may occur over time. Such a diffusion of components into the adhesive may alter the composition of the adhesive significantly, which in turn might impair the functional properties of the adhesive and the anti-blocking property is lost during extended storage.

Some compounded coextrusion coatings are known. Compounded coextrusion coatings are typically coextruded with the adhesive composition and typically consist of various components, which in their combination provide for the anti-blocking and anti-tacking properties of the hot-melt pressure sensitive adhesive. Problems with migration of ingredients of the compounded coextrusion coatings occurs to a lesser extended in comparison to powdered coating material, but migration of components from the compounded coextrusion coating into the hot-melt pressure sensitive adhesive composition continues to pose a major problem for compounded coextrusion coatings, especially during long-term storage.

The coextrusion coating (b) according to the present invention provides significant advantages in comparison with conventional used anti-blocking additives, which are conventionally added to the corresponding adhesive composition, such as powdered coating materials or compounded coextrusion coatings. A major difference between the different systems is that the coextrusion coating (b) according to the present invention is applied to the hot-melt pressure sensitive adhesive composition (a) during the coextrusion process, by coextruding a hot-melt pressure sensitive adhesive composition (a) together with the coating (b). Thereby, the coextrusion process according to the present invention does not require an additional step of adding anti-blocking agents, but instead allows for the provision of the packaged hot-melt adhesive according to the present invention in a one-step process.

Another important aspect of the coextrusion coating (b) of the present invention is that the coating consists of "neat" polymers.

Without being bound to a specific theory, it is believed that the effectiveness of the anti-blocking properties of the coextrusion coating (b) is a result of the chemical and physical characteristics of the neat coating film materials. This is supported by the fact that the coextrusion coating (b) is not penetrated over time during storage and migration of adhesive components into the coating is avoided. Also, with the use of neat polymer extrusion coatings, deterioration of anti-blocking properties of the coating by migration of components of the coating composition into the adhesive is excluded. In this regard it is noted that conventional powdered coated hot-melt compositions during storage at high room temperatures (25-70° C.) tend to "absorb" the anti-tack powders, thus deteriorating the anti-tack effectiveness. It was observed that this does not happen with the coextruded coating (b).

Furthermore, some of the conventional anti-blocking agents such as silica create inhalable dusts that are potentially harmful or can cause serious health issues, for example lung or respiratory problems. The coextruded coating (b) is not inhalable. This reduces health risks and expenses for filters and air cleaning equipment. Consequently, coextruded coating (b) provide a favorable, environmentally friendly and safe alternative to silica as an anti-blocking agent for individual forms of packaged hot-melt adhesives.

A particular advantage of the "neat" coating polymers in comparison to previously used anti-tack coatings is that uniform "neat" coating material can be designed and manufactured, which can be applied to different adhesive compositions. Conventional anti-tack coatings have the disadvantage that the type and amount of components present in said anti-tack coatings have to be separately adjusted for each individual type of adhesive composition to meet their specific properties. In contrast, the "neat" coating polymers according to the present invention encompass a single component, which does not diffuse into the adhesive composition, and could therefore be pre-designed and manufactured in large quantities, and be subsequently applied to a large variety of different adhesive compositions. Therefore, the use of "neat" coating polymers according to the present invention provides a resource- and cost-efficient way to provide coextrusion coatings for packaged hot-melt adhesives.

In one aspect of the present invention, the packaged hot-melt adhesive comprises a hot-melt pressure sensitive adhesive composition (a) and a coextrusion coating (b) of consisting of neat low-density polyethylene, neat polypropylene, or neat ethylene vinyl acetate having a melt flow index between about 20 g/10 min and about 300 g/10 min (ASTM D 1238-190° C., 2.16 kgs).

The term "neat" according to the present invention, which refers to neat polymers, encompasses exclusively one type of polymer, which do not contain any additional polymers, beside the stated polymers. Thereby, any blends of polymers with additional copolymers or additives are excluded from the definition of "neat" polymers according to the present invention.

A "neat" low-density polyethylene coating (b) according to the present invention refers to a low-density polyethylene with a melt flow index between about 20 g/10 min and about 300 g/10 min. Said "neat" low-density polyethylene has a room temperature density between about 0.80 g/cm$^3$ and about 1.00 g/cm$^3$, preferably between about 0.85 g/cm$^3$ and about 0.95 g/cm$^3$, more preferably between about 0.90 g/cm$^3$ and about 0.93 g/cm$^3$, even more preferably between about 0.91 g/cm$^3$ and about 0.92 g/cm$^3$ and most preferably about 0.92 g/cm$^3$. Said "neat" low-density polyethylene has a melting point between about 60° C. and about 130° C., preferably between about 80° C. and 110° C. and most preferably between about 95° C. and about 110° C., which has been determined according to the Exxon Mobil method.

Preferably, a "neat" low-density polyethylene coating (b) includes a low-density polyethylene with a melt flow index between about 20 g/10 min and about 120 g/10 min, preferably between about 20 g/10 min and about 60 g/10 min, more preferably between about 26 g/10 min and about 40 g/10 min.

Alternatively, a "neat" low-density polyethylene coating (b) may also include a low-density polyethylene with a melt flow index between about 120 g/10 min and about 300 g/10 min, preferably between about 140 g/10 min and about 160 g/10 min, more preferably between about 150 g/10 min.

A neat low-density polyethylene coating (b) with a melt flow index between about 20 g/10 min and about 300 g/10 min may be combined with any hot-melt pressure sensitive adhesive composition (a) according to the present invention, preferably with an adhesive composition (a), which comprises a base polymer selected from polyolefins, polyolefin copolymers, polyolefin/alpha-olefin interpolymers, more preferably selected from the group consisting of ethylene and propylene homo- or copolymers.

Also preferably, a neat low-density polyethylene coating (b) according to the present invention may be combined with an adhesive composition (a), which comprises a base polymer selected as metallocene-synthesized polymer, preferably a metallocene-synthesized ethylene or propylene homo- or copolymer, more preferably a metallocene-synthesized propylene polymer.

Also preferably, a neat low-density polyethylene coating (b) according to the present invention may be combined with an adhesive composition (a), which comprises a base polymer selected as ethylene vinyl acetate.

Also preferably, a neat low-density polyethylene coating (b) according to the present invention may be combined with an adhesive composition (a), which comprises a base polymer selected from synthetic rubbers.

A "neat" polypropylene coating (b) according to the present invention may also refer to a polypropylene with a melt flow index between about 20 g/10 min and about 300 g/10 min. Said "neat" polypropylene has a room temperature density between about 0.80 g/cm$^3$ and about 1.00 g/cm$^3$, preferably between about 0.85 g/cm$^3$ and about 0.95 g/cm$^3$, more preferably between about 0.88 g/cm$^3$ and about 0.92 g/cm$^3$, even more preferably between about 0.89 g/cm$^3$ and about 0.91 g/cm$^3$ and most preferably about 0.90 g/cm$^3$.

Optionally, a "neat" polypropylene coating (b) may refer to a polypropylene with a melt flow index between about 50 g/10 min and about 150 g/10 min, preferably between about 80 g/10 min and about 120 g/10 min, more preferably between about 100 g/10 min.

A neat polypropylene coating (b) with a melt flow index between about 20 g/10 min and about 300 g/10 min may be combined with any hot-melt pressure sensitive adhesive composition (a) according to the present invention, preferably with an adhesive composition (a), which comprises a base polymer selected from polyolefins, polyolefin copolymers, polyolefin/alpha-olefin interpolymers, more preferably selected from the group consisting of ethylene and propylene homo- or copolymers.

Also preferably, a neat polypropylene coating (b) according to the present invention may be combined with an adhesive composition (a), which comprises a base polymer selected as metallocene-synthesized polymer, preferably a metallocene-synthesized ethylene or propylene homo- or copolymer, more preferably a metallocene-synthesized propylene polymer.

Also preferably, a neat polypropylene coating (b) according to the present invention may be combined with an adhesive composition (a), which comprises a base polymer selected as ethylene vinyl acetate.

Also preferably, a polypropylene coating (b) according to the present invention may be combined with an adhesive composition (a), which comprises a base polymer selected from synthetic rubbers.

A "neat" ethylene polyvinyl acetate (EVA) coating (b) according to the present invention is ethylene polyvinyl acetate with a melt flow index between about 20 g/10 min and about 300 g/10 min. Said EVA polymer has a room temperature density between about 0.80 g/cm$^3$ and about 1.00 g/cm$^3$, preferably between about 0.90 g/cm$^3$ and about 0.96 g/cm$^3$, more preferably between about 0.91 g/cm$^3$ and about 0.95 g/cm$^3$ and most preferably about 0.935 g/cm$^3$. In the ethylene vinyl acetate the vinyl acetate content is between about 2 wt % and about 25 wt %, preferably between about 5 wt % and about 20 wt %, more preferably between about 10 wt % and about 15 wt %. Said "neat" low-density ethylene polyvinyl acetate has a melting point between about 60° C. and about 130° C., preferably between about 70° C. and about 110° C. and most preferably between about 85° C. and about 95° C. A preferred example of ethylene vinyl acetate copolymers includes Ateva 1360 available by M. Holland.

A neat ethylene polyvinyl acetate coating (b) with a melt flow index between about 20 g/10 min and about 300 g/10 min may be combined with any hot-melt pressure sensitive adhesive composition (a) according to the present invention, preferably with an adhesive composition (a), which comprises a base polymer selected from polyolefins, polyolefin copolymers, polyolefin/alpha-olefin interpolymers, more preferably selected from the group consisting of ethylene and propylene homo- or copolymers.

Also preferably, a neat ethylene polyvinyl acetate coating (b) according to the present invention may be combined with an adhesive composition (a), which comprises a base polymer selected as metallocene-synthesized polymer, preferably a metallocene-synthesized ethylene or propylene homo- or copolymer, more preferably a metallocene-synthesized propylene polymer.

Also preferably, a neat ethylene polyvinyl acetate coating (b) according to the present invention may be combined with an adhesive composition (a), which comprises a base polymer selected as ethylene vinyl acetate.

According to the present invention, the coextrusion coating (b) comprises neat low-density polyethylene, neat polypropylene, or neat ethylene vinyl acetate having a melt flow index between about 20 g/10 min and about 300 g/10 min.

The melt flow index of the coextrusion coating material correlates with its physical properties.

At low melt flow index of less than about 20 g/10 min, the coextrusion coating material displays a high viscosity and a poor melting behaviour, which leads to a partially inhomogeneous melt and at least partially prevents proper mixing of the adhesive components.

On other hand, a high melt flow index of more than 300 g/10 min correlates with poor anti-blocking properties, e.g. barrier properties, of the corresponding packaged adhesive, which in turn leads to individual forms, which tend to agglomerate during the melting process and are not free-flowing.

Therefore, the melt flow index between about 20 g/10 min and about 300 g/10 min of the neat low-density polyethylene, neat polypropylene, or neat ethylene vinyl acetate coating materials covers an optimal range for the coating (b) to display its properties.

The inventors surprisingly found that packaged hot-melt adhesives wherein the coextrusion coating (b) consisting of neat low-density polyethylene, neat polypropylene, or neat ethylene vinyl acetate, which comprises a melt flow index between about 20 g/10 min and about 80 g/10 min display excellent anti-blocking properties, e.g. barrier properties, which include particular forms of packaged hot-melt adhesives, which are free-flowing and or have a substantially tack-free surface for extended periods of time. It might be advantageous to combine said coextrusion coating materials, which comprises a melt flow index between about 20 g/10 min and about 80 g/10 min with a higher plasticizer content, which may be added to the hot-melt pressure sensitive adhesive composition (a).

In the present invention, the coextrusion coating (b) of the packaged hot-melt adhesives in accordance with the present invention consist of neat low-density polyethylene, neat polypropylene, or neat ethylene vinyl acetate, which comprises a melt flow index between about 20 g/10 min and about 80 g/10 min, preferably between about 20 g/10 min and about 50 g/10 min, more preferably between about 20 g/10 min and about 30 g/10 min, and most preferably about 20 g/10 min.

The inventors surprisingly found out that the packaged hot-melt adhesives consisting of neat low-density polyethylene, neat polypropylene, or neat ethylene vinyl acetate, which comprises a melt flow index between about 120 g/10 min and about 300 g/10 min display a low viscosity and an optimal normal melting behavior, leading to a homogenous melt. It may be advantageous to combine said coextrusion coating materials, which comprise a melt flow index between about 120 g/10 min and about 300 g/10 min with a reduced amount of plasticizer, which may be included in the hot-melt pressure sensitive adhesive composition (a).

In the present invention, the coextrusion coating (b) of the packaged hot-melt adhesives in accordance with the present invention consist of neat low-density polyethylene, neat polypropylene, or neat ethylene vinyl acetate, which comprises a melt flow index between about 150 g/10 min and about 300 g/10 min, preferably between about 170 g/10 min and about 280 g/10 min, more preferably between about 180 g/10 min and about 250 g/10 min, and most preferably about 220 g/10 min.

The coextrusion coating (b) at least partially, preferably substantially completely, covers the surface of the hot-melt pressure sensitive adhesive composition (a), e.g. by a film layer on the surface of the hot-melt individual forms. For the purpose of the present invention, the term "at least partially covers" means that at least 10%, preferably more than 25%, more preferably more than 50%, and most preferably more than 75% or more than 90% of the surface of the individual forms are covered by the coextrusion coating (b) in accordance with the present invention. Most preferably, the coextrusion coating (b) completely covers the surface of the hot-melt pressure sensitive adhesive composition (a).

In particular, the coextrusion coating (b) consists of a crystalline material, which tends to be come easily meltable. Preferably, the coextrusion coating (b) has a high crystallinity.

In one embodiment, the coextrusion coating (b) may be present in an amount between about 0.1 wt % and about 5 wt %, referring to the total weight of the packaged hot-melt adhesive. Preferably, the coextrusion coating (b) may be present in amount between about 0.5 wt % and about 3 wt %. More preferably, the coextrusion coating (b) may be present in amount between about 1.0 wt % and about 3.0 wt %. In an even more preferred embodiment, the co-extrusion coating (b) may be present in amount between about 1.5 wt % and about 3.0 wt %. In an even more preferred embodiment, the co-extrusion coating (b) may be present in amount between about 1.5 wt % and about 2.5 wt %. In a most preferred embodiment, the co-extrusion coating (b) may be present in amount between about 1.5 wt % and about 2.0 wt %, referring to the total weight of the packaged hot-melt adhesive.

If the base polymer present in the hot-melt pressure sensitive adhesive composition (a) is selected as a synthetic rubber, the coextrusion coating (b) may be present in an amount between about 0.5 wt % and about 3 wt %, preferably, between about 1.0 wt % and about 3.0 wt %, more preferably between about 1.5 wt % and about 3.0 wt %, even more preferably between about 1.5 wt % and about 2.5 wt % and most preferably between about 1.5 wt % and about 2.0 wt %, referring to the total weight of the packaged hot-melt adhesive.

If the base polymer present in the hot-melt pressure sensitive adhesive composition (a) is selected as a polyolefin, polyolefin copolymer, polyolefin/alpha-olefin interpolymer, the coextrusion coating (b) may be present in a higher amount in relation to the amount of coating (b) present if the base polymer is selected as a synthetic rubber, preferably in an amount between about 0.1 wt % and about 5 wt %, more preferably between about 0.5 wt % and about 4 wt %, even more preferably between about 1.0 wt % and about 3 wt %, even more preferably between about 1.0 wt % and about 2.5 wt %, even more preferably between about 1.0 wt % and about 2.0 wt % and most preferably between about 1.5 wt % and about 2.0 wt %, referring to the total weight of the packaged hot-melt adhesive.

The coextrusion coating (b) may have a melting temperature between about 60° C. and 170° C., between about 60° C. and about 150° C., preferably between about 100° C. and about 140° C. and more preferably between about 120° C. and about 130° C. The melting temperature has been measured according to the Ring and Ball softening point method (DIN EN 1427).

The coextrusion coating (b) may have a room temperature density between about 0.80 g/cm$^3$ and about 1.00 g/cm$^3$, preferably between about 0.91 g/cm$^3$ and about 0.93 g/cm$^3$ and more preferably about 0.92 g/cm$^3$.

C. Individual Forms

The packaged hot-melt adhesives according to the present invention may be in any form suitable for their use, including any "individual forms", irrespective of size. For the purpose of the present invention the term "individual forms" comprise packaged hot-melt adhesives in the form of granules, blocks, pillows, prills. For another purpose of the present invention the term "individual forms" comprise elongated ropes or rods, or any other known form of hot-melts. The elongated ropes or rods can be of any length, and, e.g., can be wound onto a reel, spool or can be freely laid inside a box or other container and applied from there. Preferred "individual forms" such as blocks, pillows, elongated ropes or rods may have a size, in the longest dimension, in the range of centimeters, for example up to about 15 cm or up to about 20 cm. In certain embodiments, the packaged hot-melt adhesives are in the form of smaller sized "individual forms", such as particles, prills, chips, flakes, spheres, beads, slugs, e.g. sausage shaped slugs, or pellets.

The "individual forms" may be selected from a plurality of pillows or prills. A "prill" in the meaning of the present invention refers to a substantially spherical bead, while a "pillow" refers to a substantial prismatic geometric object, such as obtained by cutting off pieces from a cylindrical strand, which optionally contains rounded edges and/or corners. In a preferred embodiment, said pillows may have a substantial prismatic rectangular form with average dimensions (length/width/height) of about 40 mm×about 30 mm×about 12 mm, or about 20 mm×about 20 mm×about 20 mm. In a more preferred embodiment, said pillows may have average dimensions (length/width/height) of about 40 mm×about 20 mm×about 10 mm, most preferably of about 40 mm×about 15 mm×about 7 mm.

An individual form can weigh less than about 15 grams, or even less than about 10 grams.

Alternatively, the pillows may have a substantially cube like form. Also such pillows may have rounded corners, thereby forming almost a spherical shape.

In another embodiment of the present invention, the "individual forms" are selected from at least one of coextruded ropes or rods, which do can be of any length. Preferably, the coextruded ropes or rods may have a length between about 1 m and about 100 m, and more preferably between about 5 m and about 50 m. In a preferred embodiment, the coextruded ropes or rods may have a diameter between about 0.1 cm and about 5 cm, preferably between about 1 cm and about 3 cm, and more preferably about 2.5 cm. Preferably the coextruded ropes or rods are wound onto a reel or spool or are freely laid inside a box or other container.

According to the present invention, the packaged hot-melt adhesive has a substantially tack-free surface and/or is free-flowing, preferably for extended periods of time, such as a month, 3 months, 6 months, a year, or more than a year. The packaged hot-melt adhesive may have a tack-free surface and/or may be free-flowing at ambient conditions or room temperature, i.e. at temperatures from about 20° C. to about 25° C., and/or at elevated ambient temperatures, i.e. at temperatures from about 25° C. to about 70° C. The term "free-flowing" as used in the present invention means that "individuals" of the packaged hot-melt adhesive are able to move freely and without any difficulty and/or any agglomeration. Included in the definition "free-flowing" individuals are individuals, which do not fuse together and/or are able to move freely with none or minimal mechanical action and/or are mechanical separable.

E. Preparation of Individual Forms of a Packaged Hot-Melt Adhesive

The individual forms of a packaged hot-melt adhesive according to the present invention comprise a hot-melt pressure sensitive adhesive composition (a), which is covered by a coextrusion coating (b). The inventive individual forms, particularly pillows or ropes may be substantially tack-free and/or free-flowing.

According to one embodiment of the present invention, a method for preparing individual forms of a packaged hot-melt adhesive according to the present invention comprises the first step of providing a hot-melt pressure sensitive adhesive composition (a), and the second step of coextruding said adhesive composition (a) together with a coating (b) in such way that the coating (b) at least partially covers the surface of the hot-melt pressure sensitive adhesive composition (a), thereby forming the individual forms of the packaged hot-melt adhesive and optionally cutting the individual forms into pillows or prills.

The inventive method allows the preparation of tack-free and/or free flowing individual forms of the packaged hot-melt adhesive.

Individual forms of the packaged hot-melt adhesive, particularly pillows or prills, may be particularly suitable for use e.g. in vacuum feeders or similar conveying equipment due to their small size and weight. However, due to the larger surface of pillows or prills compared to larger blocks, pillows or prills may have a higher tendency to agglomerate. Thus, the present invention is specifically advantageous with small sized forms such as pillows or prills, although it may equally work with pellets, flakes, blocks or any other form of individuals of the inventive packaged hot-melt adhesive.

The production of the individual forms of the packaged hot-melt adhesive, e.g. pillows or prills, may require multiple passes through a co-rotating twin screw extruder to homogenize the hot-melt pressure sensitive adhesive composition (a), followed by an coextrusion of the adhesive composition (a) together with the coating (b) through a coextrusion system, followed by a solidifying process optionally followed by the calibration of the granules size.

Preferably, the packaged hot-melt adhesive according to the present invention is obtained by a coextrusion process, wherein the hot-melt pressure sensitive adhesive composition (a) is pumped through the coextrusion head and wherein the coextrusion coating (b) is added to the adhesive composition (a) such that the coextrusion coating (b) substantially covers the adhesive composition (a) as a cover sheet.

Furthermore, the packaged hot-melt adhesive is obtained by a coextrusion process, wherein the coextrusion process comprises:
(i) providing one or more hot-melt components and blending the hot-melt components to form a hot-melt pressure sensitive adhesive composition
(ii) providing a coating material selected from neat low-density polyethylene, neat polypropylene, or neat ethylene vinyl acetate having a melt flow index between about 20 g/10 min and about 300 g/10 min.
(iii) coextruding both (i) and (ii) such that the adhesive forms a strand substantially surrounded by the coating material
(iv) optionally cutting the resulting, coated strand of adhesive (e.g. by forcing the composition past rotating blades and cutting the hot-melt ribbons to form resultant individual forms)
(v) solidifying the individuals, optionally by cooling the individuals by a liquid cooling medium or by a dry air circulated.

Preferably, the individuals produced from this method are pillows or prills.

Hot-melt pressure sensitive adhesive compositions are suitable for preparing the inventive hot-melt individuals as described above. Optionally, the packaged hot-melt adhesive individuals may comprise additional components such as described above.

E. Use of Individual Forms

In one aspect of the present invention, a plurality of individual forms of a packaged hot-melt adhesive according to the present invention may be used in an adhesive application process, wherein the packaged hot-melt adhesive is conveyed to a melting system in a free-flowing and/or air conveyable form before being molten and applied to a substrate.

A disadvantage of individual forms of packaged hot-melt adhesives previously used is that said particular forms may fuse together inside the adhesive containing containers, e.g. during storage. Such fusion of individual forms may occur, when said individual forms are conventionally bulk packaged, e.g. packaged in huge quantities in pouches or boxes. The elevated temperature, which may be present in warehouses, combined with the weight of the pouches themselves, if stacked upon each other, may cause that the conventional individual forms fuse together into a large entity or agglomerate. This complete fusion of individual forms may result in that the corresponding packaged hot-melt adhesives may not be used in an adhesive application process, e.g. by conveying the packaged hot-melt adhesive to a melting system, a feeder or the like.

Therefore, it is an object of the present invention to provide individual forms of the packaged hot-melt adhesive, which do not tack or fuse together during the shipping or storage both at room temperature, as well as elevated temperatures. It is a further object of the present invention to modify the coextrusion coating (b) of the packaged hot-melt adhesive to obtain individual forms of the adhesive which have a significantly reduced fusion/blocking tendency, such that said individual forms stay loose and/or can be easily separated. It is a further object of the present invention to improve the individual forms of packaged hotmelt adhesives, in such a way that these adhesives can be packaged and automatically processed during an adhesive application process, i.e. during conveying said individual forms during a melting process.

The individual forms of the package hot-melt adhesive according to the present invention do not tack or fuse together in a storage device at 45° C. and remain substantially loose and free-flowing.

The term "substantially loose" means that the particles do not stick together or may be easily separated from each other if temporarily blocking, by application of mechanical forces such as kicking against the container or vibration, or any other suitable methods.

With the packaged adhesive of the present invention, the plurality of individual forms does not fuse together as determined by a blocking test.

In one embodiment of the present invention the individual forms of the packaged hot-melt adhesive may be stored in an adhesive containing container, e.g. a cardboard carton, a box, preferably a plastic box, a plastic bag, a pouch, a big bag or a supersack. These containers might contain between about 100 kg and about 1,000 kg of individual forms, preferably between about 400 kg and about 1,000 kg.

One aspect of the present invention encompasses an adhesive containing container, comprising a plurality of individual forms of the packaged adhesive according to the present invention, wherein the container is selected from at least one of a box, preferably a plastic box, plastic bag, a pouch, a big bag, and a supersack.

The term "big bag" as used herein also encompasses the terms "super sack", or "bulk bag", which could be alternatively used in the context of the present invention, and refers to bags made of textile or other flexible material usable for shipping, handling and storing of flowable products. Such big bags are commercially available from e.g. PEMA Verpackung GmbH, Germany, preferably PEMA Article number 40-09999hb, in various sizes and are conventionally used for larger amounts of individual materials, such as greater 100 kg to metric tons. Such big bags also include reusable, recyclable and/or returnable versions of big bags.

In one embodiment, the adhesive containing package bag comprises sealed bags. In a preferred embodiment, the adhesive containing package bag may be chosen as a conical bottomed bulk bag/supersack or full drop or open bottom system, protected with s-flaps bulk bag/supersack. Preferably, said bags are made from out of coated 180+30 gr./sqm pp-woven-fabric.

In a typical adhesive application process, the individual forms are provided from the container into a melting system, wherein said individual form are being transferred to the melter, wherein the individual forms are molten and applied to a substrate.

In one embodiment of the present invention, the plurality of individual forms is conveyed to the melting system by vacuum conveying, tubular drag conveying, a big bag conveying method, melt on demand, or any combination thereof.

The vacuum conveying system is depicted in FIG. 1 and includes packaged hot-melt pressure sensitive adhesive which is inserted, e.g. by a big bag (1), into a feed hopper (2) and the vibratory feeder (3). A vacuum pump (4) generates a vacuum in the vacuum conveyors separator tanks (5) and thereby sucks in air through the inlet point at the feed hopper (2), which in turn causes the packaged hot-melt adhesive to be aspirated and carried in the corresponding air stream. Inside the separator tanks (5), a filter unit (6) separates the packaged hot-melt adhesive from the air, wherein the adhesive is contained in the separator tanks (5). When the separator tanks (5) are filled with adhesive, the vacuum pump switches off, the pressure in the separator tanks is adjusted to the surrounding pressure and the adhesive material is discharged through a discharge valve (7) directly into the hot-melt tank (8) to be charged. The discharge step is controlled by a load cell (9), which determines that the desired amount of adhesive is loaded into the hot-melt tanks (8). After the discharge step, the discharge valve (7) directly closes and the complete conveying cycle restarts again.

An exemplary tubular dragconveying method, which refers to a disc conveying system according to Cablevey Company, US, is depicted in FIG. 2 and consists of a pipe (4) with the diameter of from about 7 cms to about 13 cms, typically about 10 cm, through which the individual forms (6) are conveyed. The pipes are preferably stainless steel. The super sack (1) containing individual forms (6) can be discharged into a conical bottom feed hopper (2). Below the hopper discharge (2) is an inclined vibratory feeder (3). It can be useful to put a limit switch on the vibratory feeder to control the rate at which the individual forms are fed into the tubular drag conveying system If the individual forms are fed in too quickly, blockages can occur. When the level in the adhesive melt tank (8) drops, the level transmitter sends a signal to a controller and the controller then activates the vibratory feeder (3). Individual forms will flow out of the hopper (2), down the vibratory feeder (3) and into the tubular drag conveyor system. This system consists of a drive motor, pulleys and a cable (7). Every about 15 cm to about 20 cm, along the length of the cable (7) are positioned plastic discs (5) that are roughly about 10 cm in diameter. The pillows (6) fill in the voids between the discs (5). The discs (5) are pulled slowly through the pipe line (4), conveying the individual forms (6) toward the melt tanks (9). The system can feed multiple melt tanks (9). Above each melt tank (9) is a rotating valve and drop section of pipe (8), down to the melt tank (9). If that tank level is calling for feed, the valve spins (8) open and the pillows (6) fall into that melt tank (9). When the level in the melt tank reaches a "full" set point, the controller/load cell (10) signals the valve (8) to spin closed and the flow of pillows to that tank stops. If the other melt tanks (9) on this same system are also full, then the controller/load cell (10) will also turn off the vibratory feeder (3) and the disc conveyor system. When the next melt tank requires additional adhesive the system turns on and completes the next cycle of feed. This tubular drag conveying system is very gentle on the individual forms, and this is important because the individual forms should not be damaged in any conveying system, or risk to spill out the adhesive and gumming up the feed system.

It has been found that when using a tubular dragconveying system for conveying individual adhesive forms, running at a lower than maximum capacity provides sufficient throughput while decreasing the possibility of adhesive plugs. The tubular drag conveying system can be run at less than about 50% capacity, less than about 30% capacity, less than about 20% capacity or even from about 5% to about 50% capacity.

The individual form conveyed in the tubular drag conveying method can be a pillow. In embodiments, it is helpful if the pillow has a minimum thickness to prevent getting squeezed between the disc and the wall of the tube. It is useful if the pillow has a thickness of greater than about 0.318 cms (0.125 inches), at least about 0.635 cms (0.250 inches), or even from about 0.635 cms (0.250 inches) to about 1.2 cms (0.472 inches).

An exemplary big bag conveying method according to the present invention involves an adhesive containing container, selected e.g. as a big bag or supersack, wherein the adhesive content of the container is manually or automatically, e.g. by a crane or forklift, placed above a conical feed hopper. Typically, the big bag or supersack may contain manufactured fracture sites in the material, which may cause the material to fracture, such that the big bag or supersack opens up at a defined location, e.g. at the bottom of the bag. The fractures sites are typically generated in a way that the fracture only occurs upon a specific impulse, e.g. by pulling a rope, which is attached to the fracture sites. By opening the bottom of the supersack, the adhesive flows into the canonical feed hopper and from there directly into the pre-melter or into a further conveying system to reach the pre-melters. In the further adhesive application process, a fully or partially working automated system similar to the systems described in the vacuum and tubular drag conveying method described above may be employed.

An exemplary melt on demand conveying method according to the present invention involves the individual forms being fed into an extruder (i.e. a single screw extruder) or other melting apparatus and then pumped through a heated hose into at least one melt tank and optionally many melt tanks found on separate manufacturing lines in the same location. Optionally, the molten adhesive can be fed directly in to one or more adhesive nozzles. The individual forms can be fed into the extruder in any possible way including by use of a vibratory feeder.

In the present invention, the individual forms used in the vacuum, tubular drag and/or big bag conveying system according to the present invention are selected from the group consisting of pillows, prills, flakes or chips, preferably pillows.

Another aspect of the vacuum, tubular drag conveying and melt on demand methods of the present invention is to avoid cross contamination. During a manual feeding process of individual forms of the packaged hot-melt adhesive, there is a possibility that the operator might feed the wrong grade of adhesive or a different adhesive into the melt tank. In the above described automated conveying system, a bar coding or scanning element may be included in the system that will alarm and minimize the likelihood of using the wrong adhesive.

Another aspect of contamination is to allow ambient plant dust to enter the melt tanks. This could result in "charring" and discoloration of the hot-melt adhesive as it's applied to the customer's product. Every time the operator now opens the lid on the hot-melt tank, dust or other foreign could enter the tank. The above-described automatic feed system would essentially be a closed system, thus minimizing the occurrence of contamination. With the current, manual feed practice, the melt tank levels are typically cycled from full to fairly empty until being refilled. This results in a thin film of adhesive along the walls of the heated tanks that are exposed to significant heat history and could result in charring of the adhesive over time. In the described automatic feed system, the level of adhesive is automatically controlled to maintain the level consistently thereby avoiding high and low levels, and thereby minimizing the thin film heat history.

F. General Use of Packaged Adhesive

The packaged hot-melt adhesive according to the present invention can be used in the production of typical nonwoven hygiene articles, sanitary devices, care articles, disposable medical drapes, paper, packaging, tapes and labels, furniture, textiles, footwear, in woodworking or in construction industries e.g. for roofing membranes or for other construction type lamination.

Further, the packaged hot-melt adhesive according to the present invention can be used in the production of nonwoven hygiene and sanitary articles, non-woven articles, labeling, elastic lamination, construction and core lamination or positioning adhesive. Also, the packaged hot-melt adhesive according to the present invention is used in the production of diapers, adult incontinence devices, sanitary napkins and disposable medical drapes.

The packaged hot-melt adhesive according to the present invention may also be used in the production of disposable articles. Preferably, the packaged hot-melt adhesive according to the present invention is used in the production of at least part of the core of the disposable article or at least part of an elastic attachment attached to the disposable article.

The invention will now be described by way of the following examples. All parts, ratios, persons and amounts stated are by weight unless otherwise specified.

EXAMPLES

In the context of the present invention, unless indicated otherwise, the melt flow index (MI) is determined in accordance with ASTM D 1238 at a standard temperature of 190° C. and at 2.16 kg load.

The viscosity is determined similar to method ASTM D-3236 as follows. The viscosity of a sample is determined using a Brookfield Laboratories DVH, DV-II, or DV-III Viscometer. The spindle used may be a SC-21, SC-27, SC-29 or SC-34 hot-melt spindle suitable for measuring viscosities in a range between about 100 mPas and about 4,000,000 mPas. The sample is placed in a pre-warmed measuring cell, which in turn is inserted into the heating element/container and is locked into place. The sample is heated until it is melted with additional sample being added until the melted sample is about 5 mm higher than the cylinder of the measuring spindle. The viscometer apparatus is lowered and the spindle is submerged into the sample. The viscometer is turned on and set to a shear rate that leads to a torque reading in the range of from 30% to 60%. Readings are taken every minute for about 15 minutes or until the values stabilize. The final reading can be obtained after 30 min and is recorded in mPas.

The molecular weight of all materials mentioned in this description, if not expressly stated otherwise, is determined by the method ASTM D 4001-93/2006.

The melting point is determined according to DIN EN 1427 (Ring and Ball) with the Ring and Ball instrument MC753 as summarized as follows. Two shouldered rings are heated to melt temperature and are placed onto a silicon-papered glass-plate and the melted substance is poured into the rings. After cooling, the excess materials were cut off and the samples were placed into the sample holder of the apparatus and the ball-centering guide with the balls is placed above the samples. A 600 ml NF beaker is filled with 500 ml Glycerin and is placed on the heating plate of the MC 753 apparatus. The frame, which is ready for measurement with the shouldered rings, is placed into the beaker in such a way that it is centered on the pins. The temperature sensor is adjusted in the therefore designed opening in the frame and the MC 753 apparatus is activated by choosing the measuring point (keyboard 1-10, basic unit). After a certain pre-heating time, the program automatically runs with a heating rate of 5° C. per minute until the balls fall. The measurement is completed when both balls have fallen down and two temperatures are shown on the display.

Polymer density is determined according to method ASTM D 1505.

The penetration number (PZ, "Penetrationszahl") is determined by needle penetration according to the test procedure is described in DIN 51579. About 100 g of sample polymer is melted until a temperature about 10 to 15° C. above the melting temperature. The homogeneous melt is filled into a corresponding examination cylinder, cooled at room temperature for about 1 hour and incubated at 25° C. for 1 hour. The melt-containing cylinder is placed in a pre-adjusted needle penetration device (mass: 100 g, time: 5 sec, temperature: 25° C.). The needle is automatically positioned at the melt surface, the measuring process is started and the penetration depth is recorded. For reproducibility three consecutive measurements are performed and the average value of the three measurements is recorded. The penetration number indicates the hardness of the polymer composition and is referred to as $\frac{1}{10}$ mm. Thereby a high penetration number refers a soft material, wherein the low penetration number refers to a hard material.

The blocking test 1 according to the present invention is performed by placing 5 kg of co-extruded individuals (e.g. pillows) of the product in 3 bags. The particular containing bags were placed at 45° C. in a forced air chamber for 2 hours. After the incubation period, the bags were stacked on top of each other. A 5 kg weight was placed on top of the stack of bags for 1 hour.

Afterwards, the weight was removed and the individual in the bags were evaluated according to the criteria set out below.

The blocking test 2 according to the present invention is performed by placing 15 kg of co-extruded individuals (e.g. pillows) of the product in a corrugated box with a lid. The box was placed at 30° C. in an oven for 1 week. After the incubation period, the box was removed from the oven and the pillows were dumped out and evaluated.

A rating system was developed, ranging from 1 to 5, to classify the potential of co-extruded individual to not block during the further application in the melting process.
1: individual forms are completely fused together
2: individual forms are mostly fused together
3: individual forms are partially fused together, cannot be separated by mechanical force
4: individual forms are partially fused together, can be separated by mechanical force
5: no fusion of individual forms observed Example 1

A packaged hot-melt adhesive was prepared by using 1 wt % low density polyethylene (LDPE) with a melt flow index of 150 g/10 min and a room temperature density of 0.913 as the coextrusion coating material on a standard hot-melt pressure sensitive adhesive having a mineral oil content of 20.6 wt % and a 15 wt % polystyrene containing linear styrene-isoprene-styrene block copolymer (MW 220,000, coupling efficiency 81%, Kraton D-1161 NS). The results are shown in Table 1 below.

Example 2

A packaged hot-melt adhesive was prepared by using 2 wt % low density polyethylene (LDPE) with a melt flow index of 150 g/10 min and a room temperature density of 0.913 as the coextrusion coating material on a standard hot-melt pressure sensitive adhesive having a mineral oil content of 27 wt % and ethylene-octene copolymer (ENGAGE 8200, Dow Chemical Company). The results are shown in Table 1 below.

Example 3

A packaged hot-melt adhesive was prepared by using 2 wt % low density polyethylene (LDPE) with a melt flow index of 150 g/10 min and a room temperature density of 0.913 as the coextrusion coating material on a standard hot-melt pressure sensitive adhesive having a mineral oil content of 16 wt % and a metallocene-synthesized low molecular weight polypropylene polymer (L-MODU S-400, Idemitsu Kosan Co., Ltd.). The results are shown in Table 1 below.

The following comparative examples are included.

Comparative Example 1

A packaged hot-melt pressure sensitive adhesive was prepared by coextruding a standard hot-melt pressure sensitive adhesive having 26.5 wt % of mineral oil and ethylene-octene copolymer (ENGAGE 8200, Dow Chemical Company) coextruded with 2 wt % of a coating composition, which in turn comprises 40.0 wt % hydrogenated microwax (Shell Microcrystalline Wax HMP, Shell), 35.9 wt % of cycloaliphatic hydrocarbon resin tackifing agent (ESCOREX 5320, Exxon Mobil Company), 23.9 wt % of styrene ethylene butylene styrene block copolymer (SEPTON 8007, Kuraray America, Inc.). The results are shown in Table 1 below.

TABLE I

|  | Example No. | | | |
| --- | --- | --- | --- | --- |
|  | 1 | 2 | 3 | Comp. 1 |
| Viscosity at 150° C. [mPas] | 2,800 | 4,800 | 5,900 | 4,800 |
| Melting point [° C.] | 93 | 94 | 104 | 94 |
| Melt index of polymer coating | 150 | 150 | 150 | — |
| Blocking test results (1)$^x$ | — | 3 | 5 | 1 |
| Blocking test results (2)x | — | 5 | — | 1 |

Blocking test results
1: individual forms are completely fused together
2: individual forms are mostly fused together
3: individual forms are partially fused together, cannot be separated by mechanical force
4: individual forms are partially fused together, can be separated by mechanical force
5: no fusion of individual forms observed According to table 1, the neat LDPE coating according to the present invention, which is used in Examples 1, 2 and 3 in an amount of 1 wt % and 2 wt % results in superior results in blocking tests compared to the conventional coating composition used in Comparative Examples 1 and 2, irrespectively of the base polymer used.

Moreover, a direct comparison of the composition of Example 2 with the composition of comparative example 1, wherein the type of base polymer and the amount of plasticizer of the hot-melt pressure sensitive adhesive are identical, shows improvement in blocking test of the neat LDPE coating in comparison with the conventional coating materials.

The following table 2 provides comparative examples A, B, C and D with examples 1, 2 and 3, and discloses different polymers, comprising varying amounts of plasticizer in relation to the corresponding penetration numbers (PZ).

TABLE II

| | | | Example No. | | | | |
|---|---|---|---|---|---|---|---|
| | Comp. A | 3 | Comp. C | Comp. D | 2 | Comp. E | 1 |
| Polymer type | Kraton D1117[1] | L-MODU S400[2] | Vector 4411[3] | Taipol SBS-320 | EG-8200[4] | Vector 4114A[5] | Kraton D1161 NS[6] |
| Plasticizer content [wt %] | 5 | 16 | 18 | 25 | 26 | 26 | 21-26 |
| PZ [25° C.] | 63 | 32 | 34 | 62 | 51 | 132 | 117 |

PZ: Penetrationszahl/Penetration number
[1]Kraton D1117 - available from Kraton Polymers U.S. LLC; 17% Styrene, MFR = 33 g/10 min @200° C., 5 kg; 33% diblock
[2]L-MODU S-400 - metallocene catalyzed polypropylene available from Indemitsu Kosan Co. Ltd. Viscosity @190 C. = 7000 cp
[3]Vector 4411A - available from Dexco Polymers; 44% Styrene, MFR = 40 g/10 min @ 200° C., 5 kg; <1% diblock
[4]EG-8200 - metallocene catalyzed ethylene octene available from Dow Chemical Company, MI = 5.0 g/10 min, 190° C., 2.16 kg
[5]Vector 4114A - SIS available from Dexco Polymers; 15% Styrene, MFR = 25 g/10 min @ 200° C., 5 kg; diblock content = 42%
[6]Kraton D 1161NS - SIS available from Kraton Polymers U.S. LLC; 15% Styrene, MFR = 9 g/10 min @ 200° C., 5 kg; diblock content = 33%

The above specific examples are not intended to limit the present invention. Rather, other embodiments are within the appended claims.

The invention claimed is:

1. A packaged-hot-melt pressure sensitive adhesive comprising a plurality of individual forms, the individual forms comprising:
   (a) a hot-melt pressure sensitive adhesive composition, and
   (b) a coextrusion coating consisting of neat low-density polyethylene, neat polypropylene or neat ethylene vinyl acetate, wherein the neat low-density polyethylene, neat polypropylene or neat ethylene vinyl acetate has a melt flow index between about 20 g/10 min and about 300 g/10 min (ASTM D1238-190° C., 2.16 kgs) and wherein the individual forms are
   obtained by a coextrusion process, wherein the coextrusion process comprises:
   i. providing one or more hot-melt components and blending the hot-melt components to form the hot-melt pressure sensitive adhesive composition,
   ii. providing the coextrusion coating,
   iii. coextruding both the hot melt pressure sensitive adhesive composition and the coextrusion coating such that the hot melt pressure sensitive adhesive composition forms a strand substantially surrounded by the coextrusion coating,
   iv. optionally cutting the resulting, coated strand of hot melt pressure senstive adhesive,
   v. solidifying the individual forms.

2. The packaged adhesive according to claim 1, wherein the adhesive composition (a) comprises a base polymer selected from the group consisting of polyolefins, polyolefin copolymers, polyolefin/alpha-olefin interpolymers and synthetic rubbers.

3. The packaged adhesive according to claim 1, wherein the adhesive composition (a) comprises a metallocene-synthesized polypropylene polymer.

4. The packaged adhesive according to claim 1, wherein the adhesive composition (a) comprises a synthetic rubber.

5. The packaged adhesive according to claim 1, wherein the adhesive composition (a) additionally comprises one or more plasticizers in an amount of less than about 20 wt %, of the total weight of the packaged adhesive.

6. The packaged adhesive according to claim 1, wherein the amount of the coating (b) is between about 1.5 wt % and about 5 wt %, referring to the total weight of the packaged adhesive.

7. The packaged adhesive according to claim 1, wherein the melt flow index of the coating (b) is between about 50 g/10 min and about 180 g/10 min.

8. The packaged adhesive according to claim 1, wherein the coating (b) has a room temperature density between about 0.90 g/cm$^3$ and about 0.93 g/cm$^3$.

9. The packaged adhesive according to claim 1, wherein the packaged adhesive has an average penetration number (PZ), which is between about 20 and about 70.

10. The packaged adhesive according to claim 1, wherein the adhesive composition (a) has a viscosity at 150° C., which is between about 500 mPas and about 10,000 mPas.

11. The packaged adhesive according to claim 1, wherein the packaged adhesive comprises a form selected from a group consisting of a pillow, a pill and a coextruded rope.

12. The packaged adhesive according to claim 11, in the form of a rope having a diameter of between about 1 cm and about 3 cms.

13. A coextruded packaged hot-melt pressure sensitive adhesive, obtained by a process wherein the hot-melt pressure sensitive adhesive composition (a) is pumped through a coextrusion head and wherein the coextrusion coating (b) is added to the adhesive composition (a) such that the coextrusion coating (b) substantially covers the adhesive composition (a) as a cover sheet and; wherein the hot-melt pressure sensitive adhesive composition has an average penetration number (PZ), which is between about 20 and about 70.

14. The coextruded packaged hot-melt pressure sensitive adhesive according to claim 13 provided as a plurality of individual forms.

15. A method of using the plurality of individual forms of a packaged adhesive according to claim 14 in an adhesive application process, wherein the packaged adhesive is conveyed to a melting system, then heated to a molten state in the melting system, and applied to a substrate.

16. The method according to claim 15, wherein the plurality of individual forms do not fuse together and/or are mechanically separable to induce free flowing of the individual forms prior to entering the melting system.

17. The method according to claim 15, wherein the plurality of individual forms is conveyed to a melting system by a conveying system selected from the group consisting of vacuum conveying, tubular drag conveying, big bag conveying and melt on demand conveying.

18. The method according to claim 15, wherein the plurality of individual fonns is conveyed to the melting system by a distribution system, which automatically distributes the plurality of forms to the melting system.

19. A method of using a packaged adhesive according to claim 1 wherein the molten adhesive is applied to a substrate in the production of an article selected from a group consisting of diapers, adult incontinence devices, sanitary napkins and medical drapes.

* * * * *